United States Patent [19]

Johnson

[11] Patent Number: 4,495,357
[45] Date of Patent: Jan. 22, 1985

[54] PYRIDYL-SUBSTITUTED-BENZOFURANS

[75] Inventor: Roy A. Johnson, Norfolk County, Mass.

[73] Assignee: The Upjohn Company, Kalamazoo, Mich.

[21] Appl. No.: 430,306

[22] Filed: Sep. 30, 1982

Related U.S. Application Data

[63] Continuation-in-part of Ser. No. 385,622, Jun. 8, 1982, abandoned, which is a continuation-in-part of Ser. No. 279,374, Jul. 1, 1981, abandoned.

[51] Int. Cl.$^3$ ............................................. C07D 405/06
[52] U.S. Cl. ..................................... 546/269; 546/270
[58] Field of Search ................................. 546/269, 270

[56] References Cited

U.S. PATENT DOCUMENTS

| | | | |
|---|---|---|---|
| 4,112,224 | 9/1978 | Bundy | 542/426 |
| 4,259,338 | 3/1981 | Paioni et al. | 424/267 |
| 4,271,170 | 6/1981 | Tanouchi et al. | 546/342 |
| 4,410,539 | 10/1983 | Cross et al. | 424/273 R |

FOREIGN PATENT DOCUMENTS

| | | |
|---|---|---|
| 50957 | 5/1982 | European Pat. Off. |
| 2537837 | 3/1976 | Fed. Rep. of Germany . |
| 2039903A | 8/1980 | United Kingdom . |

OTHER PUBLICATIONS

Vernin et al., J. Heterocyclic Chem., vol. 16, pp. 97-103, Jan. 1979.
Takamatsu et al., J. C. S. Chem. Comm., pp. 903-904 (1973).
Benzofurans, Mustafa-Wiley (1974) p. 28.
Chem. Abstracts-Chem. Substance Index (1977-1981) pp. 8283 and 8284.
D. Harris, et al., Advances in Prostaglandin and Thromboxane Research 6:437 (1980).
T. Miyamoto, et al., Advances in Prostaglandin and Thromboxane Research 6:443 (1980).
H. Tai, et al., Advances in Prostaglandin and Thromboxane Research 6:447 (1980).

*Primary Examiner*—Alan L. Rotman
*Assistant Examiner*—Bernard I. Dentz
*Attorney, Agent, or Firm*—Lawrence T. Welch

[57] ABSTRACT

The present invention provides novel pyridinyl-benzofurans and derivatives thereof which are useful as thromboxane $A_2$ ($TXA_2$) synthetase inhibitors and as such represent potent pharmacological agents.

33 Claims, No Drawings

PYRIDYL-SUBSTITUTED-BENZOFURANS

CROSS REFERENCE TO RELATED APPLICATIONS

This application is a continuation in part of copending application Ser. No. 385,622 now abandoned, filed June 8, 1982, which is a continuation in part of Ser. No. 279,374, filed July 1, 1981, now abandoned.

BACKGROUND OF THE INVENTION

The present invention relates to novel compositions of matter. More particularly, the present invention relates to pyridyl substituted benzofurans. These compounds are potent thromboxane $A_2$ inhibitors and as such represent useful pharmacological agents.

Since the discovery that human platelets convert the prostaglandin endoperoxide ($PGH_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, "Biological and Pharmacological Evaluation of Thomboxane Synthetase Inhibitors," Advances in Prostaglandin and Thromboxane Research, 6:417 (1980), and references cited therein. Most important are compounds which selectively inhibit $TXA_2$ synthetase. Id.

PRIOR ART

A number of $TXA_2$ synthetase inhibitors are known. See for example the bi-heterocyclic 9,11-trideoxy-PGF-type compounds disclosed in U.S. Pat. No. 4,112,224; SQ 80,388 [1-(3-phenyl-2-propenyl)-1H-imidazole] disclosed in D. Harris, et al., Advances in Prostaglandin and Thromboxane Research 6:437 (1980); pyridine and its derivatives, disclosed in T. Miyamoto, et al., Advances in Prostaglandin and Thromoboxane Research, 6:443 (1980), and British patent application No. 2,039,903A (abstracted in Derwent Farmdoc No. 50111C (1980)). See also H. Tai, et al., Advances in Prostaglandin and Thromboxane Research, 6:447 (1980). Other compounds which have been disclosed as thromboxane synthetase inhibitors, include sodium p-benzyl-4(1-oxo-2-(4-chlorobenzyl)-3-phenylpropyl)-phenyl phosphate, imidazoles, nordihydroguaiaretic acid, and 12L-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

Tetrahydropyridinyl- and piperidinyl-substituted benzofurans are disclosed in U.S. Pat. No. 4,259,338 as psychopharmaceuticals and antidepressants. Similar compounds are disclosed in German Offenleggunschrift No. 2,537,837.

SUMMARY OF THE INVENTION

Thus, the present invention particularly provides: a compound of the formula I wherein $Z_1$ is
(a) 4-pyridinyl,
(b) 3-pyridinyl, or
(c) 3-pyridinyl substituted at the 4 position by
 (1) methyl,
 (2) $-OCH_3$,
 (3) $-N(CH_3)_2$, or
 (4) $NH_2$, or
 (5) at the 2, 4, 5, or 6 position by chlorine;
wherein $X_1$ is
 (a) $-(CH_2)_n-$,
 (b) $-CH(OH)-$, or
 (c) $-C(O)-$;
wherein $R_1$ is hydrogen, a pharmacologically acceptable cation, ($C_1-C_{12}$) alkyl, ($C_3-C_{10}$) cycloalkyl, ($C_7-C_{12}$) aralkyl, phenyl, phenyl mono-, di-, or trisubstituted by chloro, ($C_1-C_3$) or alkyl, or phenyl para-substituted by
 (a) $-NHCO-R_{25}$,
 (b) $-O-CO-R_{26}$,
 (c) $-CO-R_{24}$,
 (d) $-O-CO-(p-Ph)-R_{27}$, or
 (e) $-CH=N-NH-CO-NH_2$,
wherein $R_{24}$ is phenyl or acetamidophenyl, $R_{25}$ is methyl, phenyl, acetamidophenyl, benzamidophenyl, or amino, $R_{26}$ is methyl, phenyl, amino or methoxy; and $R_{27}$ is hydrogen or acetamido, and wherein $-(p-Ph)$ is 1,4-phenylene;
wherein $R_7$ is
 (a) hydrogen,
 (b) $-CH_2OH$,
 (c) $-COOR_1$,
 (d) $-CH_2N(R_4)_2$,
 (e) $-CN$,
 (f) $-CON(R_4)_2$, or
 (g) $-C(O)-R_4$;
wherein $R_4$ is
 (a) hydrogen,
 (b) ($C_1-C_4$)alkyl, or
 (c) phenyl;
wherein $R_9$ and $R_{12}$ are the same or different and are
 (a) hydrogen,
 (b) ($C_1-C_4$)alkyl
 (c) fluoro,
 (d) chloro,
 (e) bromo,
 (f) $-OCH_3$, or,
 (g) when taken together and attached to contiguous carbon atoms, $-O-CH_2-O-$;
wherein D represents a single or a double bond; and wherein m is an integer 0 to 4, inclusive; and wherein n is an integer 0 to 1, inclusive; including, pharmacologically acceptable acid addition salts thereof; and when D represents a single bond, an enantiomer or a racemic mixture of enantiomers thereof.

The carbon atom content of various hydrocarbon-containing moieties is indicated by a prefix designating the minimum and maximum number of carbon atoms in the moiety, i.e., the prefix ($C_i-C_j$) indicates a moiety of the integer "i" to the integer "j" carbon atoms, inclusive. Thus ($C_1-C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine,
4-ethylmorpholine,
1-isopropylpyrrolidine,
2-methylpyrrolidine,
1,4-dimethylpiperazine,
2-methylpiperidine, and the like, as well as amines containing water-solubilizing or hydrophilic groups, e.g., mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
glactamine,
N-methylglycamine,
N-methylglucosamine,
ephedrine,
phenylephrine,
epinephrine,
procaine, and the like. Further useful amine salts are the basic amino acid salts, e.g., lysine and
arginine.

Examples of suitable pharmacologically acceptable quaternary ammonium cations are tetramethylammonium,
tetraethylammonium,
benzyltrimethylammonium,
phenyltriethylammonium, and the like.

Pharmaceutically acceptable acid addition salts are formed at the heterocyclic amine moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art, e.g., as depicted in Example 8.

The compounds of the present invention will be named herein as benzofurans, using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention were tested for $TXA_2$ inhibition as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which selectively inhibit $TXA_2$ synthetase are found. For a discussion of $TXA_2$ synthetase inhibition testing see, e.g., R. Gorman, supra.

Using this test system, one compound, ethyl 5-(3'-pyridinylmethyl)benzofuran-2-carboxylic acid, sodium salt (Example 2), has been shown to be the most effective in inhibiting $TXA_2$ formation. This compound has an approximate $ED_{50}$ in this system of 10 ng/ml.

The novel compounds of this invention have thus been shown to be highly active as selective inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 63409B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, dogs, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg to about 500 µg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$, $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biology, in the Journal of Cell Biology, 87:64 (1980).

Similarly, prostacyclin has been shown to be an effective antihypertensive agent. The compounds of the present invention are also used for this purpose. (See, e.g., British patent specification No. 2,039,903A).

For a general discussion of the utility of $TXA_2$ synthetase inhibitors which increase endogenous prostacyclin, see, Aiken, et al. J. Pharmacol. Exp. Ther., 219:299 (1981).

The compounds of the present invention are prepared by the methods depicted in Charts A–L.

Thus, the compounds of the present invention wherein m is zero are prepared by the method of Chart A. In Chart A, $R_{10}$ is all substituents within the scope of $R_1$ excluding the pharmacologically acceptable cations. All other variables in Chart A are defined as above. A hydroxybenzaldehyde of the Formula X is cyclized into the compounds of the present invention by methods known in the art. See, e.g., S. Tanaka, J. Am. Chem. Soc., 73:872 (1951). Thus, the compound may be reacted with diethyl bromomalonate in the presence of potassium carbonate to yield the desired benzofuran-2-carboxylic acid ester. See, e.g., D. T. Witiak, et al., J. Med. Chem. 21:833 (1978). Higher yields are obtained when the reaction conditions are changed so that the compound is reacted in the presence of sodium hydride in toluene (solubilized with dicyclohexyl-18-crown-6). Both of these procedures are set out more fully in Example 1. Conversion of the ester of the Formula XV to the desired pharmacologically acceptable salts or free acid is accomplished by known methods.

The compounds of the Formula X are well known and readily available compounds, and may be prepared from known benzylpyridines of the Formula XX as depicted in Chart B. (See, also, British patent application No. 2,039,903A.)

Referring to Chart B, a compound of the Formula XX, wherein all variables are defined as above, is nitrated by methods well known in the art, for example, treatment with nitric acid. (While the para nitro compound is the predominant product, the meta and ortho nitro compounds are also formed in smaller quantities. The desired isomer is separated by known methods.) The nitro function is easily reduced by treatment with hydrogen over a 5% palladium-on-carbon catalyst, to form a Formula XXII amine. This amino group is replaced by a hydroxyl moiety via diazotization followed by decomposition of the diazonium salt in hot aqueous acid. Formylation of this phenol to obtain the hydroxybenzaldehyde of the Formula XXIV is accomplished by modification of the Duff reaction (see, J. Duff, J. Chem. Soc. 547 (1941)), by the use of hexamethyltetramine in trifluoracetic acid, see, W. E. Smith, J. Org. Chem., 37:3972 (1972).

For compounds wherein m is one, the method of Chart C is used. An ester of the Formula XL is reduced with lithium aluminum hydride in ether or tetrahydrofuran to yield the corresponding alcohol after workup. This alcohol is tosylated or mesylated using p-toluenesulfonyl chloride or methanesulfonyl chloride in pyridine to yield the Formula XLII product. (Ts indicates the tosylated compound, but the compound could also be mesylated). This compound is treated with excess sodium cyanide in dimethylformamide (DMF) and stirred under nitrogen at room temperature for 5 hr to yield the Formula XLIII cyano compound. This compound is dissolved in ethanol and treated with 25% aqueous potassium hydroxide to yield the corresponding acid. This compound is esterified by means well known in the art, e.g., treatment with diazomethane in methanol for the methyl ester. Pharmacologically acceptable salts are also prepared by means well known in the art.

Chart D depicts the synthesis of compounds of the present invention wherein m is 2, 3, or 4. In Chart D, q is zero, one, or 2. An ester of the Formula L is reduced with diisobutylaluminum hydride (DIBAL) in toluene or methylene chloride at low temperature to yield, after workup, the Formula LI aldehyde. Reaction of this aldehyde with an alkoxy alkylene-triphenylphosphorane of the formula $Ph_3P=CHCH_2-(CH_2)_qCOOR_{10}$ (wherein Ph is phenyl) yields the unsaturated ester of the Formula LII after workup. Careful reduction of this unsaturated ester by reaction with one equivalent of hydrogen over palladium-on-carbon in alcohol yields the saturated ester of the Formula LIII. The free acid or a pharmacologically acceptable salt of this ester is prepared by means well known in the art. The corresponding amides, phenacyl esters, and the like are prepared by the methods depicted in e.g., U.S. Pat. Nos. 4,292,445 and 4,172,206. Example 7 also shows the preparation of an amide.

The dihydrobenzofurans are prepared as depicted in Chart E. A solution of a formula LX benzofuran in water is stirred with excess sodium amalgam (NaHg) for 24 hr. After workup there is obtained the corresponding Formula LXI dihydrobenzofuran. (See, e.g., D. T. Witiak, et al., J. Med. Chem. 14, 754 (1971).)

Reduction of the corresponding acid or ester of the formula $COOR_{10}$ with lithium aluminum hydride as depicted in Chart C, (XL to XLI) is used to prepare all of the corresponding alcohols within the scope of Formula I. This is seen in Example 3. Conversion of the alcohol to a corresponding acid addition salt is accomplished by known means as seen in Example 4.

The compounds of this invention wherein m is zero and $R_7$ is hydrogen are prepared by the method of Chart F, which is described more fully in Preparation 18 and Example 22. A formula LXXV aldehyde is reacted with an appropriate Wittig reagent (prepared by reacting sodium hydride and dimethylsulfoxide with an alkoxyalkyltriphenyl phosphonium halide) to yield the formula LXXVI enol ether. This compound is treated with perchloric acid to yield the formula LXXVII benzofuran.

Chart G depicts an alternate method for preparing the compounds of this invention. An ethyl-benzofuran-2-carboxylate of the formula XCVI is prepared from the corresponding XCV aldehyde by the methods described above. This compound is alkyl chlorinated by treatment with paraformaldehyde and zinc chloride to yield the formula XCVII compound. This compound is formylated by known methods, (e.g., reaction of sodium metal with ethanol followed by the addition of the XCVII compound) to yield the formula XCVIII compound. The reaction of the formula XCVIII compound with 3-lithiopyridine (prepared, e.g., by reaction of 3-bromopyridine with n-butyllithium) yields the formula CI compound wherein $X_1$ is —C(OH)—. (Preparation 7 describes a similar method using 3-methoxy-4-benzyloxybenzaldehyde.)

Chart H depicts a method for preparing chloropyridinyl compounds of this invention. This method is described more fully in Preparation 5a and Example 9. The CV pyridinyl derivative is treated with m-chloroperbenzoic acid to yield the corresponding CVI N-oxide. The N-oxide is treated with phosphorous oxychloride to yield the corresponding chloropyridyl isomers of the formula CVII.

Substituted benzofurans (i.e. compounds wherein $R_9$ and $R_{12}$ are other than hydrogen) are prepared by the methods depicted in Charts I and J.

Chart I depicts a method for preparing brominated derivatives. An aldehyde of the formula CX (prepared by the method of Chart B, see formula XXIV) is treated with bromine to yield the corresponding brominated compound of the formula CXI, which is then converted to the compounds of the present invention by the method of Chart A. This is more fully described in Preparation 9 and Example 17.

Chart J depicts a method for preparing methyl or methoxy substituted benzofurans. In Chart J, $R_{19}$ is methyl or methoxy. The formula CXV ether is hydrolyzed (using hydrobromic acid for example) to yield the formula CXVI alcohol. Similarly, the formula CXV' ether is hydrogenolyzed with hydrogen over palladium on carbon catalyst to yield the formula CXVI alcohol. This alcohol is treated with trifluoroacetic acid in the presence of hexamethylenetetramine to yield the formula CXVII aldehyde, which is converted to the compounds of this invention by the method of Chart A.

Various substituted hydroxy benzaldehydes are available commercially or may be prepared by methods known in the art. The hydroxybenzaldehydes are thus converted to the claimed benzofurans by the methods of Charts A and G.

Chart K depicts a method for preparing compounds wherein $X_1$ is —C(O)—, as described more fully in Example 8. A compound of the formula CXX is treated with potassium superoxide to yield the formula CXXI compound.

Hydrogenolysis of compounds wherein $X_1$ is —C(OH)— is depicted in Chart L. A compound of the formula CLV is hydrogenated using, e.g., a Parr apparatus and a palladium-on-carbon catalyst. This is depicted in Preparations 7, 13, and 17.

Compounds where $Z_1$ is 4-methylpyridine are prepared by converting the corresponding 4-chloropyridine of Chart H with methyl magnesium halides to the 4-methyl pyridine derivative according to the procedure described in K. Thomas and D. Jerchel, in "Newer Methods of Organic Chemistry," Vol. III., W. Foerst, ed., Academic Press, N.Y. 1964, pp 74–75.

The 4-methoxy, 4-amino, and 4-N,N-demethylamino derivatives are prepared from the corresponding 4-methoxy-3-bromopyridine (see T. Talik, Roczniki Chem, 36:1465 (1962)), 3-bromo-4-aminopyridine (see T. Talik, Roczniki Chem., 37:69 (1963)) and 3-bromo-4-dimethylaminopyridine (see J. M. Essery and K. Schofield, J. Chem. Soc., 4953 (1960)), respectively, using the procedure of Chart I (conversion of XCVIII to CI).

Preparation of various other benzofuran derivatives within the scope of this invention are prepared by analogous procedures well known in the art.

Certain compounds of the present invention are preferred. Thus, compounds of the formula I, wherein D denotes a double bond, $X_1$ is $-(CH_2)_n-$ (wherein n is zero or one, more preferably one), $Z_1$ is 3-pyridinyl, m is zero, $R_7$ is $COOR_1$, $R_1$ is Na or H and $R_9$ and $R_{12}$ are hydrogen are preferred. Compounds having all these preferences are more preferred. Thus, sodium 5-(3'-pyridinylmethyl)benzofuran-2-carboxylate is the most preferred compound of this invention.

DESCRIPTION OF THE PREFERRED EMBODIMENTS

The present invention is seen more fully by the Examples given below.

PREPARATION 1

3-(3'-Formyl-4'-hydroxybenzyl)pyridine

Refer to Chart B. (Conversion of XXIII to XXIV).

A solution of 3-(4'-hydroxybenzyl)pyridine (2.038 g., 0.011 mole) and hexamethylenetetramine (1.61 g., 0.0115 mole) in trifluoroacetic acid (20 ml) is stirred and heated in an 80° oil bath for 4 hrs. Excess trifluoroacetic acid is removed under reduced pressure. Water (35 ml) is added to the residue and the resulting solution is allowed to stand for 20 min. at room temperature. The solution is adjusted to pH~7 by the addition of solid sodium bicarbonate. A gummy oil precipitates. The mixture is extracted with ethyl acetate (3×), the extract solution is dried over $MgSO_4$, filtered, and concentrated under reduced pressure. The crude product is chromatographed over silica gel (130 g) packed as a slurry in 1:1 acetone-hexane. Elution is with the same solvent and fractions of 150 ml volume are collected. The titled product (1.263 g, 0.00593 mole, 54% yield) is obtained in fractions 5-7 as a colorless, crystalline solid. Recrystallization from acetone-hexane gives colorless crystals, mp 129°-132° C. A second recrystallization gives 3-(3'-formyl-4'-hydroxybenzyl)pyridine, mp 130°-132° C.; NMR ($CDCl_3$) peaks are observed at δ 9.89, 8.55, 6.70-7.66, and 3.98. The IR spectrum (mull) reveals peaks at 2560, 1670, 1610, 1595, 1580, 1505, and 1480 $cm^{-1}$.

The Carbon:Hydrogen:Nitrogen (C:H:N) ratio is 73.54:5.27:6.19.

PREPARATION 2

2-Hydroxy-4-[2-(3'-pyridinyl)ethyl]benzaldehyde

Refer to Chart B. (Conversion of Formula XXIII to XXIV).

1.69 g (8.49 mmol) of the phenol prepared in Preparation 6 in a flask with hexamethylenetetramine (1.26 g, 9 mmol) is dissolved in trifluoroacetic acid (10 ml) and heated in an 80° C. oil. TLC analysis after 45 min reveals that no starting material remains. The reaction is cooled to room temperature and the trifluoroacetic acid is removed under reduced pressure. The residue is stirred for 20 min with 15 ml of water. The mixture is made slightly basic with saturated $NaHCO_3$ and solid $NaHCO_3$ and extracted well with ethyl acetate (5×). The ethyl acetate layers are pooled, washed twice with water, dried ($Na_2SO_4$), filtered and evaporated to give 2.00 g of a yellow oil. The oil is chromatographed on 130 g of silica gel packed as a slurry with 50% acetone-hexane. Elution is with 50% acetone-hexane followed by 75% acetone-hexane with 1% triethylamine added. 0.170 g of the titled product are obtained.

The solid is recrystallized twice from ether-pentane to yield 91 mg of white crystals with a melting point of 93°-94° C.

Anal. Calcd. for $C_{14}H_{13}NO_2$: C, 73.99; H, 5.77; N, 6.16. Found: C, 73.57; H, 5.81; N, 5.28. Repeat: C, 73.34; H, 5.84; N, 6.94.

High resolution mass spectroscopy reveals the following:

Calcd. for $C_{14}H_{13}NO_2$: 227.0946. Found: 227.0950. Other peaks at m/e 199, 135, 107, and 92.

The NMR ($CDCl_3$, δ) peaks observed are 9.85, 8.45, 7.66-6.68, and 2.94.

PREPARATION 3

3-(4'-Nitrobenzyl)pyridine

Refer to Chart B (conversion of Formula XX to XXI).

3-Benzylpyridine (13.52 g, 0.080 mole) and nitric acid (70%, 100 ml) are stirred at 50° C. for 6 hr. The solution is poured into ice-water (1500 ml). The mixture is made alkaline by the careful addition of 50% aqueous sodium hydroxide and then extracted 4 times with 300 ml of ether. The extracts are washed with brine, dried ($MgSO_4$), filtered, and concentrated. The crude product is crystallized from acetone-hexane giving 5.67 g of 3-(4'-nitrobenzyl)pyridine. The filtrate is concentrated and the residue is chromatographed in two equal portions (4.66 g each) over two Merck size C Lobar columns. The columns are eluted with 50% ethyl acetate-hexane. A less polar product [1.83 g, 3-(2'-nitrobenzyl)-pyridine], mixed fractions (1.67 g), and additional 3-(4'-nitrobenzyl)pyridine (2.55 g) after crystallization from acetone-hexane, total 7.92 g, 0.037 mole, 46%). Two recrystallizations from acetone-hexane gives the titled product as colorless needles, having a melting point of 87°-88° C.

The C:H:N ratio is 67.33:4.77:13.23.

From the mixed fractions, 3-(3'-nitrobenzyl)-pyridine is also obtained.

PREPARATION 4

3-(4'-Aminobenzyl)pyridine

Refer to Chart B (conversion of Formula XXI to XXII).

A solution of 3-(4'-nitrobenzyl)pyridine of Preparation 8 (7.924 g, 0.0370 mole) in methanol (100 ml) is shaken with 5% Pd on carbon and hydrogen in a Parr apparatus. Hydrogen uptake is complete within 45 min. The catalyst is removed by filtration through sintered glass. The solvent is removed under reduced pressure. The crystalline residue is recrystallized from methylene chloride-hexane with a first crop of 5.229 g; a second crop of 0.492 g; a third crop of 0.480 g; and a fourth crop of 0.137 g (total 6.338 g, 0.0347 mole, 94%). Recrystallization from $CH_2Cl_2$-hexane gives colorless crystals of the titled product with a melting point of 121°-123° C.; IR (nujol) peaks are observed at 3400, 3300, 3200, 1640, 1610, 1590, 1575, 1515, 1480, 845, 800, and 710 $cm^{-1}$.

The C:H:N ratio is 77.91:6.53:15.02.

PREPARATION 5

3-(4'-Hydroxybenzyl)pyridine

Refer to Chart B (conversion of Formula XXII to XXIII).

A solution of sodium nitrite (0.350 g) in water (1.5 ml) is cooled in ice, and added, with stirring, to a cold (ice-bath) solution of 3-(4'-aminobenzyl)pyridine (Preparation 10, 0.920 g, 0.0050 mole) in water (3.75 ml), concentrated sulfuric acid (2.5 ml), and ice (7 g). This solution in turn is added dropwise to a third solution of water (5 ml) and sulfuric acid (6.25 ml) that is maintained at 160° C. in an oil bath. The resulting solution is kept at 160° C. for 10 min and then cooled to room temperature. The pH of the solution is adjusted to 7.0 by addition of aqueous 50% sodium hydroxide. The resulting mixture is extracted 4 times with 25 ml of ether. The aqueous portion is further extracted continuously with ether for 40 hr. The ether extracts are washed with brine, dried over MgSO$_4$, filtered, and concentrated under reduced pressure. The crystalline residue is decolorized with activated charcoal and is recrystallized from acetone-hexane, giving a first crop (0.426 g) of the titled crystals, with a melting point of 182°–185° C. A second crop (0.034 g) and third crop (0.050 g, total 0.510 g, 0.00276 mole, 55%) of titled crystals are also obtained. Recrystallization of the first crop from acetone-hexane gives the titled product as colorless crystals with a melting point of 184°–186° C. IR (nujol) peaks are observed at 2900, 2800, 2720, 2680, 2600, 1615, 1590, 1580, 1515, 1485, 1280, 1250, 845, 800, 710, and 640 cm$^{-1}$.

The C:H:N ratio is 77.97:6.12:7.66.

EXAMPLE 1

Ethyl 5-(3'-pyridinylmethyl)benzofuran-2-carboxylate (Formula I, $Z_1$ is 3-pyridinyl, $X_1$ is —CH$_2$— and is para to the oxygen, $R_9$ and $R_{12}$ are hydrogen, m is zero, D denotes a double bond, $R_7$ is COOR$_1$, and $R_1$ is ethyl)

Refer to Chart A.

Method 1

A mixture of Preparation 1 (1.26 g, 0.00592 mole), ethyl bromomalonate (1.577 g, 0.00660 mole), and potassium carbonate (1.66 g, 0.012 mole) in methyl ethyl ketone is stirred at reflux temperature for 18 hrs. The reaction is worked up by removing the solvent under reduced pressure, water is added, and the aqueous mixture is extracted 4 times with ethyl acetate. The combined extracts are washed with brine, dried over MgSO$_4$, filtered, and concentrated. The crude product is chromatographed over one Merck size B Lobar silica gel column. Acetone-hexane (1:3) is used to develop the column (a higher acetone-hexane ratio is used to dissolve the crude product for application to the column). Fractions of 25 ml volume were collected. Fractions 22–28 contain the titled product (0.464 g., 0.00165 mole, 28%), which crystallizes. Recrystallization from acetone-hexane gives a first crop of 0.367 g, having a melting point of 73°–74° C. Another recrystallization gives an analytical sample of crystals with a melting point of 73°–74° C., the NMR (CDCl$_3$, δ) peaks observed are 8.54, 7.67–7.00, 4.45, 4.10, and 1.41.

The C:H:N ratio is C, 72.52:5.47:4.71.

Method 2

A mixture of sodium hydride (1.25 g, 0.052 mole, 2.113 of a 59.6% dispersion of NaH in mineral oil, washed with hexane) in dry toluene (20 ml) is prepared. To this is added slowly a solution of aldehyde of Preparation 1 (4.26, 0.020 mole) in toluene (300 ml). Then a solution of diethyl bromomalonate (5.26 g, 0.022 mole) in toluene (20 ml) is added dropwise. Dicyclohexyl-18-crown-6 (36 drops) is added and the resulting mixture is stirred at room temperature. After stirring 20 hours, a thin film of solid that has caked on the walls of the flask is carefully scraped loose with a spatula. Stirring at room temperature is continued as TLC examination reveals that the reaction is incomplete. After 48 hrs, TLC (1:1 acetone-hexane) shows the reaction is complete with the desired less polar product the only significant material in the reaction. The reaction solution is poured onto a mixture of ice (100 ml), saturated sodium bicarbonate solution (100 ml), and brine (200 ml). The mixture is extracted three times with ethyl acetate. The combined organic extracts are washed (2×200 ml) with brine, dried over Na$_2$SO$_4$, filtered, and evaporated to give 6.57 g of a yellow oil. The oil is chromatographed over a column of silica gel (200 g) packed as a slurry in 30% acetone-hexane. The column is eluted with 30% acetone-hexane and fractions of about 200 ml volume are collected. The product is eluted in fractions 7–12 and after appropriate recrystallizations from acetone-hexane, a total of 4.62 g (0.0165 mole, 82% yield) of crystalline titled compound is obtained.

EXAMPLE 2

Sodium 5-(3'-pyridinylmethyl)benzofuran-2-carboxylate (Formula I, $Z_1$ is 3-pyridinyl, $X_1$ is —CH$_2$— and is para to the oxygen, $R_9$ and $R_{12}$ are hydrogen, m is zero, D denotes a double bond, $R_7$ is COOR$_1$, and $R_1$ is a sodium cation)

A solution of ethyl 5-(3'-pyridinylmethyl)benzofuran-2-carboxylate (0.425 g, 0.00151 mole) in methanol (15 ml) and aqueous 0.10N sodium hydroxide (15.1 ml, 0.00151 mole) is stirred at room temperature for 16 hrs. The solution is concentrated under reduced pressure giving a crystalline solid. Recrystallization from a small quantity of water and a large amount of acetone gives a first crop (0.370 g) and a second crop (0.011 g, total 0.381 g, 0.00138 mole, 92%) of the titled product as glistening colorless crystals, with a melting point greater than 300° C.

NMR (D$_2$O, δ) peaks are observed at 8,28, 7.53–6.90, and 3.62.

EXAMPLE 3

2-Hydroxymethyl-5-(3'-pyridinylmethyl)benzofuran (Formula I, $Z_1$ is 3-pyridinyl, $X_1$ is —CH$_2$—, and is para to the oxygen, $R_9$ and $R_{12}$ are hydrogen, m is zero, D denotes a double bond, and $R_7$ is CH$_2$OH)

To a mixture of lithium aluminum hydride (0.439 g) in tetrahydrofuran (20 ml), cooled under N$_2$ in an ice bath, is added dropwise a solution of ethyl 5-(3'-pyridinylmethyl)benzofuran-2-carboxylate (3.10 g) (Example 2) in tetrahydrofuran (40 ml). The ice bath is removed after 15 min and after one hr the reaction is quenched with ethyl acetate followed tetrahydrofuran-water (3:1). The mixture is filtered through Celite. The filtrate is washed with saturated aqueous sodium bicarbonate and with brine. The organic solution is dried over sodium sulfate, filtered, and evaporated giving 2.67 g. of a pale yellow oil. Following chromatography over silica gel using 50–70% acetone-hexane as an eluent, 2.491 g of pure 2-hydroxymethyl-5-(3'-pyridinylmethyl)benzofuran is obtained. The compound crystallizes and after two recrystallizations from acetone-hexane, colorless crystals, having a melting point of 89°–89.5° C., are obtained. NMR (CDCl$_3$, δ) reveals peaks at 8.40, 6.90–7.55, 6.53, 4.72, and 3.97; IR (Nujol) reveals peaks at 3189, 1616, 1599, 1579, 1470, 1450, 1442, 1263, 1234, 1189, 1114, 1073, 950, 810, and 794 cm$^{-1}$. High resolution mass spectoscopy reveals the following peaks: m/e 239.0948 (calcd for C$_{15}$H$_{13}$NO$_2$: 239.0946), 222, 210, 180, 161, and 147.

The C:H:N ratio is 75.25:5.44:5.85.

EXAMPLE 4

2-Hydroxymethyl-5-(3'-pyridinylmethyl)benzofuran Hydrochloride

Hydrogen chloride gas is bubbled through a solution of 2-hydroxymethyl-5-(3'-pyridinylmethyl)benzofuran (0.263 g) (Example 7) in dry ether. A white precipitate forms which is recrystallized from methanol-ether, giving the product (0.262 g) as colorless crystals with a melting point of 163°–166° C.

EXAMPLE 5

5-(3-Pyridinylmethyl)-2-benzofurancarboxylic Acid (Formula I, Z$_1$ is 3-pyridinyl, X$_1$ is —CH$_2$— and is para to the oxygen, R$_9$ and R$_{12}$ are hydrogen, D represents a double bond, m is 0, and R$_7$ is COOH) (The free acid of Example 1)

Aqueous 1.0N hydrochloric acid (2.0 ml, 0.0020 mole) is added to a solution of the compound of Example 2 (0.550 g, 0.0020 mole) in water (1 ml). A white solid separates immediately and, after 15 min, is collected by filtration using an extra milliliter of water to aid the transfer of the mixture. The solid is washed with water (4 ml) and dried, giving 0.458 g (0.0081 mole, 91%) of crystalline solid, with a melting point of 227°–228° C. The solid can be recrystallized from hot water or from acetone. From acetone, white crystals, melting point 229°–230° C. are obtained having the properties: IR (Nujol) reveals peaks at 1722, 1567, 1332, 1199, 1143, 1060, 804, 775, 764, and 712 cm$^{-1}$.

The C:H:N ratio is 71.11:4.32:5.49.

EXAMPLE 6

5-(3-Pyridinylmethyl)-2-benzofurancarboxylic Acid Hydrochloride (The hydrochloric acid addition salt of Example 5)

A hydrogen chloride saturated ether solution (20 ml) is added to a solution of the compound of Example 9 (0.210 g, 0.000830 mole) in acetone (375 ml). The volume of the resulting solution is reduced by removing solvent on the steam bath. When the volume reaches about 250 ml, crystals are seen. The solution is cooled on ice for two hrs and the crystals (0.165 g, 0.000571 mole, 69%) are collected and are found to have a melting point of 216°–248° C. The crystals are placed in acetone (400 ml), and another portion (20 ml) of ether saturated with hydrochloride is added. The mixture is left at room temperature several days after which 0.132 g of the titled crystals are collected, having a melting point 215°–240° C. IR (Nujol) reveals peaks at 2575, 1716, 1633, 1611, 1566, 1555, 1278, 1265, 1193, 1137, 938, 833, 819, 807, 791, 767, 761, 745, 715, and 690 cm$^{-1}$.

Anal. Calcd. for C$_{15}$H$_{12}$ClNO$_3$: C, 62.18; H, 4.18; N, 4.84.

The C:H:N ratio is 62.05:4.22:4.88.

The crystalline product dissolves in water (at room temperature) but after standing several minutes, a crystalline precipitate forms. These crystals are collected by filtration and have a melting point of 227°–229° C.

EXAMPLE 7

5-(3-Pyridylmethyl)-2-benzofurancarboxylic Acid Amide (Formula I, Z$_1$ is 3-pyridinyl, X$_1$ is —CH$_2$— and is para to the oxygen, m is zero, the D denotes a double bond, R$_7$ is —CONH$_2$, and R$_1$ is ethyl) (The amide of Example 2)

A solution of the compound of Example 1 (2.0 g, 0.0071 mole) in absolute ethanol (240 ml) saturated with anhydrous ammonia is stirred intermittently at room temperature (for a total of 100 hrs) and at reflux temperature (twice for a total of 12 hrs). The solution is resaturated with ammonia following each reflux period. The product: starting material ratio now is about 3:1. Ethanol is removed under reduced pressure and the crystalline residue is recrystallized from acetonitrile to give 1.396 g (0.00553 mole, 78%) of titled product as a white crystalline solid, with a melting point of 151.5°–152.5° C., containing no starting ester as determined by TLC. The compound is recrystallized again from acetonitrile, giving colorless crystals, with melting point 151.5°–152.5° C. The IR (Nujol) spectrum reveals peaks at 3249, 3085, 1695, 1635, 1585, 1477, 1425, 1266, 1193, 1125, 1042, 1027, 944, 937, 875, 835, 830, 770, 714 and 704 cm$^{-1}$. The NMR (CDCl$_3$, δ) spectrum reveals peaks at 8.55, 7.64–7.16, and 4.10. The mass spectrum reveals ions at m/e 252.0891, 236, 208, and 180.

The C:H:N ratio is 71:18:4.87:11.00.

EXAMPLE 8

5-(3-Pyridinoyl)-2-benzofurancarboxylic Acid (Formula I, Z$_1$ is 3-pyridinyl, X$_1$ is —C(O)— and is para to the oxygen, D represents a double bond, m is 0, and R$_7$ is COOH)

A mixture of potassium superoxide (0.20 g, 0.00282 mole) in dimethylsulfoxide (10 ml) containing dicyclohexyl-18-crown-6 (0.10 g) is stirred 30 min at room temperature. The compound of Example 1 (0.140 g, 0.00050 mole) is added directly to the mixture and stirring is continued. The reaction is followed by TLC (1:1 acetone-hexane or 75% ethyl acetate-hexane) until no starting material remains in the reaction mixture. After four hours the reaction is poured into water (75 ml) and the pH of the resulting solution is adjusted to 4–5 by addition of 1N aqueous hydrochloric acid. A white precipitate gradually forms. The solution is cooled on ice and after several hours the solid is collected by filtration. The dry solid weighs 0.049 g (0.000183 mole, 36%) and did not melt below 300° C. The solid may be crystallized from either acetic acid-water or methanol. A sample dissolved in hot glacial acetic acid and crystallized by the addition of water was submitted for analysis; IR (Nujol) reveals peaks at 1731, 1655, 1613, 1598, 1584, 1572, 1321, 1254, 1180, 1143, 1125, 1116, 1097, 1053, 754 cm$^{-1}$, mass spectrum reveals ions at 267, 222, 189, and 161 m/e.

Anal. Calcd. for C$_{15}$H$_9$NO$_4$ (267.23): C, 67.41; H, 3.39; N, 5.26.

The C:H:N ratio is 67.07:3.40:5.09.

PREPARATION 5a

Ethyl 5-(3-Pyridinylmethyl)-2-benzofurancarboxylate, N-Oxide (The N-oxide of the compound of Example 1)

Refer to Chart H (conversion of CV to CVI).

A solution of the benzofuran ester of Example 1 (563 mg, 2.0 mmol) in methylene chloride (50 ml) is treated with m-chloroperbenzoic acid (447 mg of 85% m-chloroperbenzoic acid, 2.2 mmol) and stirred at room temperature. The reaction is found to be complete after two hrs. by thin-layer chromatography on silica gel. The reaction is worked up by dilution with methylene chloride. The methylene chloride solution is washed with saturated HaHCO$_3$ solution (2×), followed by water and thin dried (Na$_2$SO$_4$). After filtration, the solvent is removed to give 621 mg of a solid. The product is recrystallized twice from acetone-hexane to give 445 mg of white crystals having a melting point of 120°-121° C.

TLC: silica gel, 10% methanol-chloroform starting material R$_f$=0.66, product R$_f$=0.42.

Anal. Calcd for C$_{17}$H$_{15}$NO$_4$: C, 68.67; H, 5.08; N, 4.71. The C:H:N ratio is 68.64:5.46:4.62.

The high resolution mass spectrum reveals: Calcd for C$_{17}$H$_{15}$HO$_4$: 297.1001 Found: 297.0994.

The IR (mull) spectrum reveals peaks at 1739, 1602, 1568, 1480, 1319, 1296, 1265, 1215, 1198, 1143, 970, 938, 895, 851, 841, 832, 805, and 758 cm$^{-1}$.

NMR (CDCl$_3$, δ) spectrum reveals peaks at 8.09, 7.27, 4.45 and 4.03.

EXAMPLE 9

5-[3-(2-Chloropyridyl)methyl]-2-benzofurancarboxylic Acid, Ethyl Ester; 5-[3-(4-Chloropyridyl)methyl]-2-benzofurancarboxylic Acid, Ethyl Ester; 5-[3-(5-Chloropyridyl)methyl-2-benzofurancarboxylic Acid, Ethyl Ester; and 5-[3-(6-Chloropyridyl)methyl]-2-benzofurancarboxylic Acid, Ethyl Ester (Formula I, Z$_1$ is 3-(2,4,5, or 6-chloropyridyl), X$_1$ is —CH$_2$— and is para to the oxygen, D is a double bond, m is zero, and R$_7$ is COOCH$_2$CH$_3$)

Refer to Chart H (conversion of CVI to CVII).

A solution of the Preparation 5a (0.878 g, 0.00295 mole) in 10 ml phosphorous oxychloride (POCl$_3$) is stirred and heated to the reflux temperature of POCl$_3$ for 30 mins. At this time TLC indicates that the desired reaction is complete. The reaction solution is poured into ice-water and ether and the pH of the aqueous phase is adjusted to aproximately 8 by the addition of solid potassium carbonate. The ether layer is separated and the aqueous phase is extracted three more times with ether. The ether extracts are pooled, washed with water, dried over sodium sulfate, filtered, and concentrated under reduced pressure. The residual oil is chromatographed over two Merck size B Lobar silica gel columns, using 20% ethyl acetate-hexane followed at fraction 113 by 40% ethylacetate-hexane to elute the column. Fractions of 25 ml are collected and the products elute in the following order of increasing polarity: the 6-chloropyridyl isomer (0.295 g, 0.00093 mole, 31%) is obtained in fractions 31–43; the 2-chloropyridyl isomer, (0.271 g, 0.00086 mole, 29%) is obtained in fractions 47–56; the 5-chloropyridinyl isomer, (0.017 g, 0.000054 mole, 2%) is obtained in fractions 79–87; and the 4-chloropyridyl isomer (0.114 g, 0.00036 mole, 12%) is obtained in fractions 145-154. After pooling the appropriate fractions and removing solvent, all the products crystallize. The individual isomers are recrystallized and analyzed as follows:

Recrystallization of fractions 31–43 from acetone-hexane gives 0.272 g of 5-[3-(6-chloropyridyl)methyl]-2-benzofurancarboxylic acid ethyl ester as colorless crystals, melting point 112°-112.5° C.; IR (Nujol) reveals peaks at 1734, 1723, 1563, 1439, 1320, 1304, 1288, 1214, 1194, 1145, 1140, 1097, 1025, 836, 812, 767, 746 cm$^{-1}$; 'N NMR (CDCl$_3$, δ) spectrum reveals peaks at 8.36, 7.18-7.65, 4.45, 4.07 and 1.42; mass spectrum reveals ions at 315.0649, (calcd for C$_{17}$H$_{14}$ $^{35}$ClNO$_3$: 315.0662) 270, 242, and 214 m/e.

Anal. Calcd. for C$_{17}$H$_{14}$ClNO$_3$: C, 64.66; H, 4.47; N, 4.44. The C:H:N ratio is 64.30:4.54:4.36.

Recrystallization of fractions 47–56 from hexane gives 0.243 g of 5-[3-(2-chloropyridyl)methyl]-2-benzofurancarboxylic acid ethyl ester, as colorless crystals, melting point 82°-83° C.; IR (Nujol) reveals peaks at 1727, 1568, 1564, 1409, 1322, 1311, 1298, 1214, 1200, 1193, 1146, 1098, 1063, 1020, 843, 811, 786, 767 cm$^{-1}$; NMR (CDCl$_3$, δ) spectrum reveals peaks at 8.32, 7.10-7.68, 4.43, 4,17, and 1.40. Mass spectrum reveals ions at 315.0658, 270, 242) and 214 m/e.

Anal. Calcd. for C$_{17}$H$_{14}$ClNO$_3$: C, 64.66; H, 4.47; N, 4.44. The C:H:N ratio is 64.53:4.49:4.35.

The crystalline fractions 79–87 of 5[3-(5-chloropyridyl)methyl]-2-benzofurancarboxylic acid ethyl ester are used for analysis without recrystallization and have melting point 90°-91° C.; NMR (CDCl$_3$, δ) spectrum reveals peaks at 8.48, 7.23-7.73, 4.48, 4.09, and 1.43. Mass spectrum reveals ions at 315.0661, 271, 242 and 214 m/e.

Recrystallization of fractions 145-154 from hexane gives 0.098 g of 5-[3-(4-chloropyridyl)methyl]-2-benzofurancarboxylic acid ethyl ester as colorless crystals, melting point 103°-104° C.; IR (Nujol) reveals peaks at 1714, 1578, 1556, 1436, 1408, 1347, 1318, 1302, 1267, 1221, 1199, 1134, 1125, 1084, 1012, 943, 882, 833, 825, 820, 804, 782, 762, 741, 695 cm$^{-1}$; NMR (CDCl$_3$, δ) spectrum reveals peaks at 8.52, 8.47, 7.23-7.73, 4.48, 4.09, and 1.43; mass spectrum reveals ions at 315.0655, 270, 242, and 214 m/e.

Anal. Calcd. for C$_{17}$H$_{14}$ClNO$_3$: C, 64.66; H, 4.47; N, 4.44. The C:H:N ratio is 64.46:4.44:4.61.

EXAMPLE 10

5-[3-(6-Chloropyridyl)methyl]-2-benzofurancarboxylic Acid, Sodium Salt (Formula I, Z$_1$ is 6-chloropyridyl X$_1$ is —CH$_2$— and is para to the oxygen, D is a double bond, m is zero, and R$_7$ is COONa)

A solution of the corresponding ethyl ester (0.221 g, 0.00070 mole) in methanol (15 ml) and aqueous 0.10N sodium hydroxide (7.3 ml, 0.00073 mole) is stirred 16 hrs at room temperature after which TLC indicates complete conversion of starting material to product. The solvent is removed under reduced pressure, leaving a white solid.

The 'N NMR (D$_2$O+CD$_3$OD, δ) spectrum reveals peaks at 8.13, 7.05-7.63 and 3.94.

EXAMPLE 11

5-[3-(2-Chloropyridyl)methyl]-2-benzofurancarboxylic Acid, Sodium Salt (Formula I, Z$_1$ is 2-chloropyridyl X$_1$ is —CH$_2$— and is para to the oxygen, D is a double bond, m is zero, and R$_7$ is COONa)

A solution of the corresponding ethyl ester (0.200 g, 0.00063 mole) in methanol (11 ml) and aqueous 0.10N sodium hydroxide (6.50 ml, 0.00065 mole) is stirred 16 hrs at room temperature. TLC (9) shows reaction is complete. Solvent is removed under reduced pressure, leaving a white solid.

'N NMR (D$_2$O+CD$_3$OD, δ) spectrum reveals peaks at 8.29, 7.87, 7.18-7.64 and 4.16.

EXAMPLE 12

5-[3-(4-Chloropyridyl)methyl]-2-benzofurancarboxylic Acid, Sodium Salt (Formula I, $Z_1$ is 4-chloropyridyl $X_1$ is —$CH_2$— and is para to the oxygen, D is a double bond, m is zero, and $R_7$ is COONa)

A solution of the corresponding ethyl ester (0.063 g, 0.00020 mole) in methanol (4 ml) and aqueous 0.10N sodium hydroxide (2.1 ml, 0.00021 mole) is stirred 16 hr at room temperature. TLC (9) shows no remaining starting material. Solvent is removed under reduced pressure leaving a white solid.

The NMR ($D_2O+CD_3OD$, δ) spectrum reveals peaks at 8.44, 8.33, 7.10–7.60 and 4.13.

PREPARATION 6

3-[(3′-Methoxy-4′-benzyloxyphenyl)hydroxymethyl]-pyridine

Refer to Chart G (analogous to conversion of XCVIII to CI).

The procedure described previously is followed using 3-bromopyridine (15.8 g, 9.64 ml, 0.10 mole), n-butyllithium (75.5 ml of a 1.6M solution 0.12 mole), and 3-methoxy-4-benzyloxybenzaldehyde (24.2 g, 0.10 mole, Aldrich Chem. Co.) in ether-THF under a nitrogen atmosphere at −78° C. After the addition of aldehyde is complete, the dry ice-acetone bath is removed and the reaction is allowed to warm. After 3 hrs, the reaction is quenched by the careful addition of a 3:1 mixture of THF-water. Additional water is added and the mixture is extracted 3 times with ether. The combined ether extracts are wased with water, with brine, and are dried over sodium sulfate. The ether solution is filtered and concentrated under reduced pressure. The residue (34 g) is combined with the crude product (33 g) from a second, identical preparation and chromatographed over silica gel (1.2 kg) packed as a slurry in 40% acetone-hexane. The crude product is applied to the column as a solution in 1:1 acetone-methylene chloride. The column is eluted with 40% acetone-hexane (25 fractions), 50% acetone-hexane (23) fractions, and then with 60% acetone-hexane. Fractions of 350 ml volume are collected. The desired product is eluted in fractions 33–59 and was obtained as a crystalline material weighing 43.14 g (0.131 mole, 65%). Recrystallization of a 2.0 g sample from acetone-hexane gives 1.88 g of the titled product as white crystals, with a melting point of 107.5°–108.5° C. A second recrystallization gives 1.80 g of white crystals, with a melting point of 107.5°–108.5° C. IR (Nujol) spectral analysis reveals peaks at 3150, 1607, 1592, 1583, 1514, 1261, 1222, 1132, 1077, 1030, 1008, 921, 862, 806, 752, 710, 701 and 670 cm$^{-1}$; the NMR ($CDCl_3$, δ) spectrum reveals peaks at 8.44, 8.25, 7.66, 6.70–7.53, 5.68, 5.08, and 3.73. The mass spectrum reveals ions at m/e 321 (M+), 230, 106 and 91.

Anal. Calcd for $C_{20}H_{19}NO_3$: C, 74.74; H, 5.96; N, 4.36. The C:H:N ratio is 74.49:6.12:4.68.

PREPARATION 7

3-Methoxy-4-(3-pyridylmethyl)phenol

Refer to Chart K (conversion of CLV to CLVI).

A solution of the compound of Preparation 6, (18.13 g, 0.056 mole) in absolute ethanol (200 ml) and 70% perchloric acid (5.1 ml, 0.056 mole) is shaken with 10% palladium on carbon (7.0 g) and hydrogen in a Parr apparatus. Uptake of hydrogen is complete after 4 hours. The catalyst is removed by filtration. Sodium bicarbonate (4.70 g, 0.056 mole) is added to the solution which then is left standing overnight. The ethanol is then removed under reduced pressure and the residue is taken up in ethyl acetate and half saturated aqueous sodium bicarbonate (40 ml). Additional water is added to dissolve a precipitated solid. The layers are separated and the aqueous layer is extracted with additional ethyl acetate. The combined ethyl acetate layers are washed with brine twice, dried over sodium sulfate, filtered, and concentrated under reduced pressure. The residue (12.03 g) is a dark red oil which crystallizes. From this and from a second reduction (of 18.53 g, 0.058 mole) there is obtained upon crystallization from ethanol 7.52 g of crystals with a melting point of 138°–141° C.

Recrystallization from acetone gives 6.36 g of titled product with a melting point of 141°–142° C. The IR (Nujol) spectrum reveals peaks at 2785–2431, 1607, 1592, 1579, 1510, 1427, 1277, 1244, 1193, 1155, 1129, 1047, 1039, 879, 819, 805, 742, and 709 cm$^{-1}$. The NMR ($d_6$-acetone) spectrum reveals peaks at 8.57δ, 8.47, 7.65, 7.30, 6.63–7.00, 3.92, and 3.80. The mass spectrum reveals ions at m/e 215.0937, 200, 184, 172, and 154.

Anal. Calcd. for $C_{13}H_{13}NO_2$: C, 72.54; H, 6.09; N, 6.51.

The C:H:N ratio is 72.61:6.17:6.51.

The filtrates and residues from the above are pooled and chromatographed over silica gel (1 kg) packed as a slurry in 35%-acetone hexane. The material is applied to the column in an acetone solution and the column is eluted with 35% acetone-hexane, collecting 350 ml fractions. From fractions 32–50, there is obtained 6.35 g (total 12.71 g, 0.059 mole, 51%) of titled product, melting point of 142°–143° C.

PREPARATION 8

2-Hydroxy-3-methoxy-5-(3-pyridylmethyl)benzaldehyde

Refer to Chart B (conversion of XXIII to XXIV).

The procedure described previously is followed using the compound of Preparation 7 (12.82 g, 0.059 mole), hexamethylenetetramine (9.11 g, 0.064 mole), and trifluoroacetic acid (125 ml). Following workup and chromatography over silica gel (RP2, 370 q, 30–40% acetone-hexane), there is obtained crystalline titled product (6.33 g, 0.026 mole, 43%) with a melting point of 114°–115° C., from acetone-hexane.

Recrystallization from acetone-hexane give colorless crystals with a melting point of 114.5°–115.5° C.; IR (Nujol) spectrum reveals peaks at 2416–2776, 1670, 1607, 1601, 1583, 1503, 1272, 1218, 1192, 1148, 1085, 987, 931, 815, 800, and 711 cm$^{-1}$. The NMR ($CDCl_3$, δ) spectrum reveals peaks at 9.98, 8.58, 7.57, 7.30, 7.02, 4.01, and 3.90. The mass spectrum reveals ions at m/e 243.0881, 215, and 214.

Anal. Calcd. for $C_{14}H_{13}NO_3$: C, 69.12; H, 5.39; N, 5.76.

The C:H:N ratio is 69.02:5.41:5.71.

PREPARATION 9

3-Hydroxy-7-methoxy-5-(3-pyridylmethyl)-2,3-dihydrobenzofuran-2,2-dicarboxylic Acid, Diethyl Ester Refer to Chart A (conversion of X to XIII).

Using the procedure of preceeding Examples the following quantities of reagents are used: sodium hydride (0.624 g, 0.026 mole, 1.05 g of a 59.6% suspension in mineral oil) in toluene (10 ml), the above aldehyde of Preparation 8 (2.43 g, 0.010 mole) in toluene (150 ml), diethyl bromomalonate (2.63 g, 0.011 mole) in toluene (10 ml), and dicyclohexyl-18-crown-6 (0.415 g). The reaction is followed by quenching aliquots in aqueous NaHCO$_3$ and ethyl acetate with TLC examination of the ethyl acetate layer. After 48 hr, the reaction appears to contain about 1:1 starting material and a single product and is not progressing further. The reaction is worked up as previously described and the crude extract is chromatographed over two Merck size B Lobar silica gel columns. The sample is applied to the columns in methylene chloride solution and the column is eluted with ethyl acetate, collecting 25 ml fractions. Fractions 22–30 contained the new product (1.21 g, 0.00302 mole, 30%), fractions 31–34 contained 0.184 g of mixed products and fractions 34–54 contain 0.410 g starting materials. Recrystallization of fractions 22–30 from acetone-hexane gives colorless crystals with melting point of 140.5°–142° C. A second recrystallization gives an analytical sampe of the title crystals, melting point of 140.5°–142° C. The IR (Nujol) spectrum reveals peaks at 3004–3093, 2728, 1744, 1722, 162, 1608, 1596, 1582, 1503, 1309, 1303, 1260, 1222, 1144, 1092, 1068, 1043, 1032, 1023, 856 and 728 cm$^{-1}$. The NMR (CDCl$_3$, δ) spectrum reveals peaks at 8.42, 7.50, 7.24, 6.85, 6.70, 5.98, 4.30, 3.90, 3.83, and 1.27. The mass spectrum reveals ions at m/e 401.1483, 311, 282, 266, 254, and 241.

Anal. Calcd. for C$_{21}$H$_{23}$NO$_7$: C, 62.83; H, 5.78; N, 3.49.

The C:H:N ratio is 62.65:5.94:3.47.

PREPARATION 10

3-Hydroxy-7-methoxy-5-(3-pyridylmethyl)-2,3-dihydrobenzofuran-2,2-dicarboxylic Acid, Disodium Salt (Conversion of Preparation 9 to its sodium salt)

A solution of the compound of Preparation 9 (0.100 g, 0.00025 mole) in methanol (4 ml) and aqueous 0.10N sodium hydroxide (5.5 ml, 0.00055 mole) is stirred 2 hr at room temperature after which time no remaining starting material is detected by TLC. The solvent is removed under reduced pressure giving a white solid. The NMR (D$_2$O, δ) spectrum reveals peaks at 8.32, 7.64, 7.30, 6.91, 6.86, 5.63, 3.92, and 3.84. A 54 mg sample is recrystallized (or repreceipitated) from methanol-water, giving 30 mg of titled product. The IR (Nujol) spectrum reveals peaks at 3271, 1645, 1624, 1574, 1503, 1354, 1322, 1291, 1237, 1142, 1066, 1042, 1027, 1015, 878, 797, 738 and 718 cm$^{-1}$.

EXAMPLE 13

7-Methoxy-5-(3-pyridinylmethyl)-2-benzofurancarboxylic Acid Ethyl Ester (Formula I: Z$_1$ is 3-pyridinyl, X$_1$ is —CH$_2$— and is para to the oxygen, R$_9$ is 7-methoxy, R$_{12}$ is hydrogen, D is a double bond, m is zero, and R$_7$ is —COOCH$_2$CH$_3$)

Refer to Chart A (conversion of XIII to XV).

A solution of the compound of Preparation 9 (0.818 g, 0.00204 mole) in dry tetrahydrofuran (THF, 20 ml) is added dropwise to a stirred mixture of sodium hydride (0.049 g, 0.00204 mole, 0.082 g of a 59% dispersion in oil) in THF (2 ml) kept under an atmosphere of nitrogen. The reaction is stirred for 1 hr. After one hr, additional sodium hydride (0.049 g) and THF (20 ml) are added. Dicyclohexyl-18-crown-6 (0.10 g) is also added at this point. After about two hr following the initial additions of reactants, TLC shows roughly equal amounts of starting material and a new material assumed to be product. Sixteen hrs later, no further change is observed in the ratio of starting material and final product so the reaction is diluted with an additional 150 ml of THF. This had little effect on the ratio of compounds. After 72 hr, the reaction is again diluted with THF (200 ml). The reaction is complete within one hr after this final dilution. The reaction mixture is poured into a solution made up of brine (100 ml) and saturated aqueous sodium bicarbonate (100 ml) together with some ice. The layers are separated and the aqueous phase is extracted four times with ethyl acetate. All organic extracts are pooled, washed twice with 50% brine, dried (Na$_2$SO$_4$), filtered, and concentrated under reduced pressure. A pale yellow oil (0.569 g) was obtained and is chromatographed over one Merck size B silica gel Lobar column. The sample is applied to the column as a solution in acetone-methylene chloride. The column is eluted with 30% acetone-hexane and fractions of 25 ml volume are collected. The desired material (0.253 g, 0.00081 mole, 40%) is eluted in fractions 31–36 and crystallized. One recrystallization from acetone-hexane gives 0.225 g of titled product as colorless crystals, with a melting point of 98.5°–99.5° C. The IR (Nujol) spectrum reveals peaks at 1728, 1600, 1569, 1321, 1295, 1273, 1201, 1153, 1146, 1095, 1031, 1021, 991, 951, 944, 891, 842, 787, 769, 745, and 719 cm$^{-1}$. The NMR (CDCl$_3$, δ) spectrum reveals peaks at 8.60, 7.54, 7.51, 7.27, 7.08, 6.80, 4.42, 4.04, 3.96, and 1.38.

The mass spectrum reveals ions at m/e 311.1169, 296, 282, and 266.

Anal. Calcd. for C$_{18}$H$_{17}$NO$_4$: C, 69.44; H, 5.50; N, 4.50.

The C:H:N ratio is 69.43:5.61:4.43.

EXAMPLE 14

7-Methoxy-5-(3-pyridylmethyl)-2-benzofurancarboxylic Acid Sodium Salt (Formula I: Z$_1$ is 3-pyridinyl, X$_1$ is —CH$_2$— and is para to the oxygen, R$_9$ is 7-methoxy, R$_{12}$ is hydrogen, m is zero, D is a double bond, and R$_7$ is —COONa)

A solution of the compound of Example 13 (0.175 g, 0.00056 mole) in methanol (6 ml) and aqueous 0.10N sodium hydroxide (6.2 ml) is stirred at room temperature 4 hr. The methano is removed under reduced pressure and the aqueous solution remaining is lyophilized, giving 0.169 g of titled product as a white powder. The IR (Nujol) spectrum reveals peaks at 3379, 1617, 1600, 1574, 1479, 1330, 1268, 1210, 1143, 1028, 993, 938, 845, 815, 791, 786, 744, and 716 cm$^{-1}$. The NMR (D$_2$O, δ) spectrum reveals peaks at 8.27, 7.46, 7.2, 6.78, 6.62, 3.86, and 3.76.

PREPARATION 11

3-Bromo-2-hydroxy-5-(3-pyridylmethyl)benzaldehyde

Refer to Chart I (conversion of CX to CXI).

Bromine (0.54 ml, 1.59 g, 0.010 mole) is added dropwise over a period of 1–2 min to a stirred solution of 2-hydroxy-5-(3-pyridinylmethyl)benzaldehyde (2.13 g, 0.010 mole) in glacial acetic acid (50 ml). As the addition of bromine is completed, orange crystals are seen to be forming in the reaction mixture. The mixture is stirred 30 min at room temperature and then filtered to allow collection of the crystalline solid. (1.865 g are obtained after air drying on the filter). The filtrate is concentrated, giving a partially crystalline residue. TLC (75% ethyl acetate in hexane) shows unreacted starting material remaining in the residue (a sample is quenched in aq. NaHCO$_3$ and ethyl acetate for TLC). The residue is mixed with acetic acid (25 ml) and stirred. Bromine (0.2 ml) is added. After stirring 30 min, the additional orange crystals that had formed are collected (2.179 g). The crystals dissolve in acetone with loss of their orange color. Crystallization is attempted by addition of hexane but only gives a greenish solid mass. Finally, the solvent is removed, the residue is taken up in water, and the pH of the aqueous solution is adjusted to approximately 7 by addition of sodium carbonate. The resulting mixture is extracted once with ether and 4 times with ethyl acetate. The pooled organic extract solutions are washed with brine, dried (MgSO$_4$), filtered, and concentrated under reduced pressure. The residue is taken up in acetone (in which it is not completely soluble) and chromatographed over silica gel (65 g) packed as a slurry in 1:1 acetone-hexane. Fractions of 25 ml volume are collected. The desired product is found in fractions 12-22 and is a crystalline solid. Recrystallization from acetone-hexane gives a first crop of yellow crystals (0.919 g) with a melting point of 87°-88° C. A second crop of pale yellow crystals (0.212 g, total crystals, 1.131 g, 0.0045 mole, 45%), melting point of 114°-115° C., is obtained. Upon recrystallization from acetone-hexane, the crystals from the first crop gave pale yellow crystals with a melting point of 115°-116° C. The IR (Nujol) spectrum reveals peaks at 1650, 1575, 1476, 1468, 1440, 1311, 1302, 1239, 1136, 1027, 835, 739, 720, and 695 cm$^{-1}$. UV (EtOH) at 0.01856 g/l reveals 221 m$\mu$ ($\epsilon$=21,600), 258.5 (11,550), 263 (12,350), 342 (3,000), and 400 (1,750) at 0.00742 g/l 220 (20,250), 263 (12,250), 268 sh (10,600), 345 (2.750), and 399 (3,250). The mass spectrum reveals ions at m/e 293, 291, 265, 263, 212, 184, and 154.

Anal. Calcd. for $C_{13}H_{10}BrNO_2$: C, 53.45; H, 3.45; N, 4.80; Br, 27.36.

The C:H:N:Br ratio is 53.42:3.67:4.72:27.41.

EXAMPLE 15

7-Bromo-5-(3-pyridylmethyl)-2-benzofurancarboxylic Acid Ethyl Ester (Formula I: $Z_1$ is 3-pyridinyl, $X_1$ is —$CH_2$— and is para to the oxygen, $R_9$ is 7-bromo, $R_{12}$ is hydrogen, m is zero, D is a double bond, and $R_7$ is COOCH$_2$CH$_3$)

Refer to Chart A.

A solution of potassium t-butoxide (0.6 ml, 1.6-1.8M in THF) is added in portions to a stirred solution of Preparation 11 (0.292 g, 0.0010 mole) in THF (8 ml). A pale yellow precipitate forms over a period of several min. The mixture is stirred 20 min and then a solution of diethyl bromomalonate (0.247 g, 0.00103 mole) in THF (5 ml) is added dropwise. The mixture is stirred one hr after the addition is completed and after this time conversion of the starting phenol to a more polar material is nearly complete as detected by TLC. Sodium hydride (0.045 g of a 59% suspension in oil, 0.026 g, 0.0010 mole) is added to the stirred mixture. No significant change in the reaction is observed and after 4 hr additional sodium hydride (0.045 g of the suspension) is added. This, and additional THF (10 ml), has little effect on the reaction during a period of 12 hr and only after addition of potassium t-butoxide (0.6 ml of THF) does the polar intermediate change to the less polar, desired product. The reaction is quenched one hr after addition of the K-t-OB$\mu$ by pouring into cold brine and saturated sodium bicarbonate. The aqueous phase is extracted with ethyl acetate 4 times. The combined extracts are washed with brine, dried over sodium sulfate, filtered, and concentrated under reduced pressure. The crude product (0.357 g) is chromatographed over one Merck size B Lobar silica gel column using 25% acetone-hexane to elute the column. Fractions of 25 ml volume are collected. A minor component (0.19 g, 0.000049 mole, 5%) is obtained in fractions 23-26. This material crystallizes and from the NMR spectrum is assigned the structure of 7-bromo-5-(3-pyridylmethyl)-2-benzofurancarboxylic acid, t-butyl ester. The NMR (CDCl$_3$, $\delta$) spectrum reveals peaks at 8.58, 7.17-7.60, 4.05, and 1.62.

The desired product is eluted in fractions 30-35, giving 0.201 g (0.000556 mole, 55%) of crystalline material. Recrystallization from acetone-hexane gives 0.169 g of 7-bromo-5-(3-pyridylmethyl)-2-benzofurancarboxylic acid, ethyl ester as colorless crystals, with a melting point of 109°-110° C. The IR (Nujol) spectrum reveals peaks at 1702, 1582, 1574, 1424, 1366, 1303, 1215, 1134, 1088, 1018, 762, 735, and 715 cm$^{-1}$. The NMR (CDCl$_3$, $\delta$) spectrum reveals peaks at 8.56, 7.13-7.60, 4.44, 4.05 and 1.40. The mass spectrum reveals ions at m/e 361, 359, 333, 332, 331, 330, 316, 314, 280, 252, 207, and 178.

Anal. Calcd. for $C_{17}H_{14}BrNO_3$: C, 56.68; H, 3.92; N, 3.89; Br, 22.19. The C:H:N:Br ratio is 56.52:3.90:3.79:22.33.

EXAMPLE 16

7-Bromo-5-(3-pyridylmethyl)-2-benzofurancarboxylic Acid Sodium Salt (Formula I: $Z_1$ is 3-pyridinyl, $X_1$ is —$CH_2$— and is para to the oxygen, $R_9$ is 7-methyl, $R_{12}$ is hydrogen, m is zero, D is a double bond, and $R_7$ is —COONa)

A solution of the compound of Example 15 (0.108 g, 0.00030 mole) in methanol (5 ml) and aqueous 0.10N sodium hydroxide (3.0 ml, 0.00030 mole) is stirred at room temperature overnight. TLC evidence (1:1 acetone-hexane) indicates complete consumption of the starting ester. The solvent is removed under pressure. The glassy residue crystallizes. The product is scraped from the flask and used as such.

The IR (Nujol) spectrum reveals peaks at 3359, 1634, 1620, 1614, 1602, 1577, 1572, 1337, 1198, 1128, 1028, 939, 871, 798, 743, and 709 cm$^{-1}$.

PREPARATION 12

3-(4-Methoxy-3-methyl)phenylhydroxymethylpyridine

Refer to Chart G (analogous to the conversion of XCVIII to CI).

The procedure described in Example 34 is followed using 3-bromopyridine (24.2 g, 14.7 ml, 0.15 mole), n-butyllithium (93.8 ml of a 1.6M solution in hexane, 0.15 mole), and 3-methyl-p-anisaldehyde (25.0 g of 90% purity, 22.5 g, 0.15 mole) in ether under a nitrogen atmosphere at −78° C. The reaction is allowed to warm to room temperature over a 3 hr period and the product is washed as previously described. The crude product is chromatographed over silica gel (1.5 kg) packed as a slurry in 35% acetone-hexane. The column is eluted with 40% acetone-hexane (22 fractions) and 50% acetone-hexane (to end) with 350 ml fractions collected. The product (26.26 g, 0.114 mole, 76%) is obtained in fractions 23-40 and is crystalline. Two recrystallizations from acetone-hexane give the title product as colorless crystals with a melting point of 92.5°-95° C. The IR (Nujol) spectrum reveals peaks at 3194, 1607, 1592, 1578, 1505, 1448, 1425, 1318, 1256, 1213, 1186, 1127, 1056, 1034, 1027, 825, 814, 745, 713, and 671 cm$^{-1}$.

The NMR (CDCl$_3$, $\delta$) spectrum reveals peaks at 8.47, 8.30, 7.74, 6.68-7.33, 5.72, 3.78, and 2.17.

The mass spectrum reveals ions at m/e 229.1115, 212, 198, 151, 123, and 106.

Anal. Calcd. for $C_{14}H_{15}NO_2$: C, 73.34; H, 6.59; N, 6.11. The C:H:N ratio is 73.51:6.68:5.96.

PREPARATION 13

3-(4-Methoxy-3-methyl)benzylpyridine

Refer to Chart K (conversion of CLV to CLVI).

The procedure for hydrogenolysis is followed using 3-(4-methoxy-3-methyl)phenylhydroxymethylpyridine (23.54 g, 0.103 mole) in ethanol (200 ml), perchloric acid (9.23 ml of a 70% aqueous solution), and 10% palladium on carbon (7 g). Following reduction and work-up, 22.38 g of an amber oil is obtained. TLC indicates that this material is of satisfactory purity for use in synthetic transformations. For analysis, a sample of the product is chromatographed over two Merck size B Lobar silica gel columns using 40% ethyl acetate-hexane for elution. The pure titled product is a colorless oil that fails to crystallize. The IR (neat) spectrum reveals peaks at 3027, 2997, 2950, 2920, 2912, 2835, 1612, 1575, 1506, 1479, 1465, 1455, 1441, 1424, 1297, 1289, 1254, 1225, 1183, 1134, 1034, 1027, 803, 741, and 712 cm$^{-1}$.

The NMR (CDCl$_3$, δ) spectrum reveals peaks at 8.50, 8.43, 7.19, 6.64–7.07, 3.84, 3.78, and 2.18. The mass spectrum reveals ions at m/e 213.1164, 198, 182, and 135.

Anal. Calcd. for $C_{14}H_{15}NO$: C, 78.84; H, 7.09; N, 6.57. The C:H:N ratio is 78.63:7.06::6.33.

PREPARATION 14

2-Methyl-4-(3-pyridylmethyl)phenol

Refer to Chart J (conversion of CXV to CXVI).

A solution of Preparation 13 (18.83 g, 0.088 mole) in aqueous 48% hydrobromic acid (50 ml) is heated for 18 hr in an 110° C. oil bath. The reaction solution is poured into ice water and the pH of the resulting solution is adjusted to about 7 by careful addition of 50% aqueous sodium hydroxide. The mixture is extracted 4 times with ethyl acetate and the pooled extracts are washed with brine, dried over sodium sulfate, filtered, and concentrated under reduced pressure. The residue (15.62 g) is a solid which is recrystallized from acetone-hexane, giving 12.29 g (0.0618 mole, 70%) of the titled product with a melting point of 165°–168° C. (capillary). Two recrystallizations from ethyl acetate-hexane give crystals having melting point of 166.5°–168.5° C. (capillary). The IR (Nujol) spectrum reveals peaks at 2713, 2676, 2579, 1740, 1611, 1592, 1588, 1512, 1480, 1435, 1425, 1273, 1262, 1245, 1213, 1186, 1143, 1120, 1046, 1033, 810, 739, 710, 645, and 630 cm$^{-1}$.

The NMR (d$_6$ acetone, δ) spectrum reveals peaks at 8.52, 8.42, 7.60, 7.27, 6.67–7.05, 3.88, and 2.16.

The mass spectrum reveals ions at m/e 199.0995, 184, 170, 154, and 121.

PREPARATION 15

2-Formyl-6-methyl-4-(3-pyridylmethyl)phenol

Refer to Chart J (conversion of CXVI to CXVII).

The procedure described previously is followed using the compound of Preparation 20 (11.0 g, 0.055 mole), hexamethylenetetramine (8.55 g, 0.061 mole), and trifluoroacetic acid (105 ml, 157 g, 1.38 mole). Following workup and chromatography of silica gel (600 g) in 30% acetone-hexane, there is obtained 5.63 g (0.0248 mole, 45%) of titled product as a crystalline solid. Two recrystallizations from acetone-hexane give colorless titled crystals having a melting point of 49°–50° C.

The IR (Nujol) spectrum reveals peaks at 1645, 1619, 1608, 1576, 1479, 1442, 1326, 1278, 1162, 1035, 1027, 834, 814, 744, 721 and 711 cm$^{-1}$.

The NMR (CDCl$_3$, δ) spectrum reveals peaks at 9.88, 8.58, 8.55, 7.55, 7.13–7.34, 3.93, and 2.24.

The mass spectrum reveals ions at m/e 227.0943 and 199.

Anal. Calcd. for $C_{14}H_{13}NO_2$: C, 73.99; H, 5.77; N, 6.16. The C:H:N ratio is 74.21:5.76:6.05.

EXAMPLE 17

7-Methyl-5-(3-pyridylmethyl)-2-benzofurancarboxylic Acid, Ethyl Ester (Formula I: $Z_1$ is 3-pyridinyl, $X_1$ is —CH$_2$— and is para to the oxygen, $R_9$ is 7-methyl, $R_{12}$ is hydrogen, m is zero, D is a double bond, and $R_7$ is —COOCH$_2$CH$_3$)

Refer to Chart A (conversion of X to XV).

The previously described procedure is followed using the compound of Preparation 21 (2.27 g, 0.010 mole), sodium hydride (0.264 g, 0.011 mole), diethyl bromomalonate (2.63 g, 0.011 mole), and dicyclohexyl-18-crown-6 (0.415 g) in a total of 210 of dry toluene. The reaction does not go to completion (TLC, 1:1 acetone-hexane) and, at various times, additional reagents (0.48 g of sodium hydride, 0.526 g of diethyl bromomalonate, 0.20 g of dicyclohexyl-18-crown-6, and 200 ml of toluene) are added without significantly affecting the reaction. After 4 days, the reaction is worked up as previously described, giving 4.43 g of an oil.

The oil (4.43 g) is dissolved in THF (300 ml) and sodium hydride (0.304 g of dispersion, 0.181 g, 0.00754 mole) is added as the dispersion in oil. Additional sodium hydride (total 0.608 g of dispersion) and THF (300 ml) are added over a period of 2 days. At this point, the desired product has formed in part and the reaction mixture is worked up with the intent of obtaining this material. The previously described workup is followed giving 4.06 g of an amber oil. The oil is chromatographed over two Merck size B Lobar silica gel columns using acetone-methylene chloride to apply the sample and 30% acetone-hexane to elute the column. Fractions of 25 ml volume are collected. The desired material (0.834 g, 0.00282 mole, 28%) is obtained in fractions 34–39 and is a crystalline solid. Two recrystallizations from hexane give colorless crystals of the titled product with melting point 100°–101° C.

The NMR (CDCl$_3$, δ) spectrum reveals peaks at 8.58, 8.53, 7.04–7.63, 4.44, 4.04, 2.54, and 1.42. The mass spectrum reveals ions at m/e 295.1200, 280, 266, 250, 222, and 194.

Anal. Calcd. for $C_{18}H_{17}NO_3$: C, 73.20; H, 5.80; N, 4.74. The C:H:N ratio is 73.07:5.93:4.68.

EXAMPLE 18

7-Methyl-5-(3-pyridylmethyl)-2-benzofurancarboxylic Acid, Sodium Salt (Formula Z-I: $Z_2$ is 3-pyridyl, $X_1$ is —CH$_2$—, and is meta to the oxygen, $R_9$ and $R_{12}$ are hydrogen, m is zero, and $R_7$ is —COONa)

A solution of the compound of Example 23 (0.500 g, 0.00169 mole) in methanol (20 ml) and aqueous 0.10N sodium hydroxide (17.5 ml, 0.00175 mole) are stirred at room temperature for six hours. Removal of solvent under reduced pressure give a pale yellow, solid residue (0.433 g recovered from flask).

The NMR (D$_2$O, δ) spectrum reveals peaks at 8.27, 6.70–7.42, 3.57, and 2.37.

PREPARATION 16

3-[(3'-Benzyloxyphenyl)hydroxymethyl]pyridine

Refer to Chart G (analogous to the conversion of XCVIII to CI).

A solution of n-butyllithium (62.5 ml of a 1.6M solution of THF, 0.10 mole) in ether (125 ml) is stirred and cooled to −78° C. To this is added dropwise over a 45-min time period a solution of 3-bromopyridine (15.8 g, 9.64 ml, 0.10 mole) in ether (125 ml). A light yellow solid precipitates from solution. The mixture is stirred and the temperature kept at −78° while adding dropwise over a period of 20 min a solution of 3-benzyloxybenzaldehyde (21.22 g., 0.10 mole) in ether (250 ml, incompletely dissolved), and 25 ml THF. Stirring is continued while allowing the bath and reaction mixture to warm to room temperature. Thin layer chromatography (30% acetone-hexane, 40% ethyl acetate-hexane) of a sample quenched in water and extracted with ether shows starting aldehyde remaining at 15 min and 2 hr but completely gone after the reaction is stirred at room temperature overnight. The rection mixture is poured into water and extracted twice with ether (500 ml). The combined ether layers are washed with brine, dried (mgSO$_4$), filtered, and concentrated. The residue is chromatographed over silica gel (500 g) packed as a slurry in 25% acetone-hexane. The column is eluted with acetone-hexane in proportions increasing from 25% to 50% of acetone. Fractions of 350 ml are collected and those containing the product (detected by TLC) are pooled. The crystalline product is recrystallized from acetone-hexane, giving a first crop of 17.785 g, melting point of 86°–88° C., a second crop of 2.025 g, melting point of 87°–88° C., and a third crop of 1.525 g (total 21.335 g, 0.073 mole, 73%). A sample of the first crop is recrystallized for analysis. The IR (Nujol) spectrum reveals peaks at 3167, 1600, 1593, 1579, 1258, 1082, 1070, 1023, 799, 740, 718, 699, and 694 cm$^{-1}$.

The NMR (CDCl$_3$, δ) spectrum reveals peaks at 8.53, 8.37, 6.8–7.9, 5.78 and 5.03.

The C:H:N ratio is 77.89:5.96:4.68.

PREPARATION 17

3-(3-Pyridylmethyl)phenol

Refer to Chart L (conversion of CLV to CLVI).

A solution of Preparation 16 (2.91 g, 0.010 mole) in absolute ethanol (150 ml) containing 5.75 ml of 2N HCl and 10% palladium on carbon (2.91 g) is shaken on a parr apparatus with hydrogen for 5¼ hr. TLC (75% ethyl acetate-hexane) shows the starting compound to be completely consumed. Catalyst is removed by filtration through a sintered glass funnel and sodium bicarbonate (solid, 1.25 g) is added to the filtrate. Solvent is removed under reduced pressure. The residue is worked up with ethyl acetate (200 ml) and water (15 ml). The aqueous layer is separated and extracted again with ethyl acetate. The combined ethyl acetate layers are washed with water, dried (Na$_2$SO$_4$), filtered, and concentrated, giving an oil (1.55 g). The oil is chromatographed over silica gel (70 g) packed as a slurry in 40% acetone-hexane. The oil is dissolved in CH$_2$Cl$_2$ for application to the column and the column is eluted with 40% acetone-hexane. Fractions of 125 ml volume are collected. The desired phenol (0.782 g, 0.042 mole, 42%) is obtained in fractions 4–6. The crystalline product is recrystallized twice from acetone-hexane, giving the titled product as colorless crystals, melting point of 117.5°–118.5° C. The IR (Nujol) spectrum reveals peaks at 3038, 2716, 2623, 1586, 1485, 1480, 1427, 1283, 1192, 1152, 1047, 873, 778, and 748 cm$^{-1}$. The NMR (CDCl$_3$, δ) spectrum reveals peaks at 8.41, 7.58, 6.60–7.25, and 3.90. The mass spectrum reveals ions at m/e 185. The C:H:N ratio is 77.86:6.33:7.55.

PREPARATION 18

2-Formyl-5-(3-pyridylmethyl)phenol and 4-Formyl-3-(3-pyridylmethyl)phenol

Refer to Chart B (conversion of XXIII to XXIV).

Using the conditions described above, the phenol of Preparation 17 (2.75 g, 0.0148 mole) is reacted with hexamethylenetetramine (2.18 g, 0.0155 mole) dissolved in trifluoroacetic acid (20 ml). Following work-up, there is obtained 2.75 g of a yellow oil which is chromatographed over slica gel (two Merck size B Lobar columns). The material is applied to the columns in CH$_2$Cl$_2$ solution and the columns are eluted with 30% acetone-hexane. Fractions of 25 ml volume are collected. Eluted first in fractions 41–42 was 4-formyl-3-(3-pyridylmethyl)phenol, (0.054 g, 0.00025 mole, 1.7%). The NMR (CDCl$_3$, δ) spectrum reveals peaks at 10.31, 8.54, 6.75–7.70, and 4.34.

The desired titled product (0.677 g, 0.00313 mole, 21%) is obtained in fractions 44–59. The crystalline material is recrystallized twice from acetone-hexane, giving the titled product as colorless crystals, melting point of 75°–76° C. The NMR (CDCl$_3$, δ) spectrum reveals peaks at 9.97, 8.58, 6.70–7.65, and 4.00. The IR (Nujol) spectrum reveals peaks at 2400–3100, 1680, 1612, 1595, 1583, 1315, 1253, 1033, 821, 748, and 710 cm$^{-1}$. The mass spectrum reveals ions at m/e 213. The C:H:N ratio is 72.81:5.51:6.44.

EXAMPLE 19

Ethyl 6-(3-pyridylmethyl)benzofuran-2-carboxylate (Formula I: $Z_2$ is 3-pyridyl, $X_1$ is —CH$_2$—, and is meta to the oxygen, $R_9$ and $R_{12}$ are hydrogen, m is zero, D is a double bond, and $R_7$ is —COOCH$_2$CH$_3$)

Refer to Chart A (conversion of X to XV).

Using the procedure described above a solution of the phenolaldehyde of Preparation 24 (0.776 g, 3.64 mmol) in toluene (60 ml), second, is added to a solution of diethyl bromomalonate in toluene (5 ml) and, third, dicyclohexyl-18-crown-6 (8 drops) to a stirred mixture of sodium hydride (0.393 g of a 59.6% suspension of NaH in mineral oil or 0.234 g of NaH, 9.75 mmol) in toluene (5 ml). The reaction is complete after stirring 90 hr at room temperature and, after work-up, there is obtained 1.17 g of crude product. This material is chromatographed over silica gel (one Merck size B Lobar column) using methylene chloride for application to the column and 25% acetone-hexane for elution. Fractions of 25 ml are collected and the desired tilted product (0.664 g, 2.36 mmol, 65%) is obtained in fractions 27–33. The crystalline product is recrystallized twice from acetone-hexane, giving an analytical sample as colorless crystals, melting point of 90°–91.5° C. The NMR (CDCl$_3$, δ) spectrum reveals peaks at 8.54, 7.10–7.70, 4.44, 4.10, and 1.40. The IR (Nujol) spectrum reveals peaks at 1726, 1621, 1563, 1480, 1371, 1325, 1299, 1219, 1190, 1147, 1098, 768, 756, 747, and 717 cm$^{-1}$. The mass spectrum reveals ions at m/e 281.1061. The C:H:N ratio is 72.21:5.36:4.85.

EXAMPLE 20

6-(3-Pyridylmethyl)benzofuran-2-carboxylic Acid, Sodium Salt (Formula I: $Z_1$ is 3-pyridyl, $X_1$ is —CH$_2$—, and is meta to the oxygen, $R_9$ and $R_{12}$ are hydrogen, m is zero, and $R_7$ is COONa) (Sodium salt of Example 19)

A solution of ester of Example 19 (0.397 g, 1.41 mmol) in methanol (15 ml) and 0.10N sodium hydroxide (14.1 ml, 1.41 mmol) is stirred at room temperature for 4 hr. TLC (50% acetone-hexane) indicates complete saponification of the ester. The solvent is removed under reduced pressure leaving a white solid. The solid is dissolved in distilled water (4 ml) and reprecipitated with the addition of acetone (250 ml). The solid, melting point greater than 280° C. (10, 0.0297 g, 1.08 mmol, 76%) is collected by filtration and dried over $P_2O_5$. The IR (Nujol) spectrum reveals peaks at 1601, 1587, 1560, 1255, 1191, 846, 803, 789, and 715 cm$^{-1}$. The NMR ($D_2O$, δ) spectrum reveals peaks at 8.22, 6.75–7.65 and 3.80.

EXAMPLE 21

6-(3-Pyridylmethyl)benzofuran-2-carboxylic Acid (Formula A-I: $Z_1$ is 3-pyridyl, $X_1$ is —$CH_2$—, and is meta to the oxygen, $R_9$ and $R_{12}$ are hydrogen, m is zero, and $R_7$ is COOH) (Free acid of Example 19)

A sample of the compound of Example 20 (0.055 g, 0.00020 mole) is dissolved in water (0.7 ml). Aqueous 1.0N hydrochloric acid (0.20 ml, 0.00020 mole) is added and the resulting white precipitate is collected by filtration, washed with water (1 ml) on the filter, and dried overnight in a vacuum dessicator, yielding 0.044 g (0.000174 mole, 87%), of product with a melting point of 222°–225° C. Recrystallization from acetone yields crystals as colorless prisms, melting point of 224°–226° C. The IR (Nujol) spectrum reveals peaks at 2382, 1713, 1294, 1230, 1187, 1098, 1051, 830, 795 cm$^{-1}$. The C:H:N ratio is 70.91:4.31:5.59.

PREPARATION 19

2-(2-Methoxyethenyl)-4-(3-pyridinylmethyl)-phenol

Refer to Chart F (conversion of LXXV to LXXVI).

Sodium hydride (395 mg of the 60% dispersion, 9.87 mmoles) is washed twice with 5 ml of dry hexane under nitrogen to remove the mineral oil. Then 8.5 ml of dry dimethylsulfoxide is added, and the stirred suspension is heated at 65° for 2 hr. The grey, homogeneous solution is cooled to 25° and treated, in one portion, with 3.38 g (9.87 mmoles) of methoxymethyltriphenylphosphonium chloride. The dark red solution is stirred for 30 min at 25°, then treated dropwise (via addition funnel) with a solution of 195 mg (0.92 mmole) of the aldehyde corresponding to the titled product in 2 ml of dimethylsulfoxide. The reaction mixture is stirred for 30 min at 25°, then poured with ice/brine/pH 7 buffer and extracted with ethyl acetate. The extracts are washed with brine, dried over anhydrous sodium sulfate, and evaporated in vacuo.

The crude product is chromatographed on an 80 g column of silica gel, packed and eluted (7 ml fractions) with ethyl acetate. Fractions 42–50 are homogeneous by TLC, and, upon combination, yield 163 mg (74% of theory) of pure enol ether. The product, which crystallizes spontaneously, is triturated with cold ethyl acetate, filtered, and dried under vacuum at 25° for 3 hr. The recrystallized enol ether weighed 95 mg and exhibited melting point 133°–135° C. (The mother liquors, 65 mg, crystallize readily and are still completely clean by TLC.) Later fractions (51–55) contain a small amount of additional enol ether, contaminated with an unknown, more polar, UV-absorbing impurity.

The IR ($\nu$max, mull) spectrum of the title compound reveals peaks at 1647, 1604, 1595, 1580, 1506, 1440, 1428, 1406, 1377, 1259, 1250, 1212, 1189, 1148, 1115, 1090, 1049, 805, 707, and 635 cm$^{-1}$.

The NMR (CDCl$_3$, δ) spectrum reveals peaks at 8.65–8.25, 7.70–6.70, 6.08, 6.00, 5.36, 5.27, 3.88, and 3.82.

The mass spectrum reveals ions at m/e 241.1129, 226, 210, 198, 180, 167, 154, 131, 115, and 92.

EXAMPLE 22

5-(3'-Pyridinylmethyl)benzofuran (Formula I: $Z_1$ is 3-pyridinyl, $X_1$ is —$CH_2$— and is para to the oxygen, $R_9$, $R_{12}$, and $R_7$ are hydrogen, D is a double bond, and m is zero)

Refer to Chart F (conversion of LXXVI to LXXVII).

A solution of 310 mg of enol ether in 10 ml of tetrahydrofuran is diluted with 150 ml of ether, and the resulting cloudy suspension is treated with 1 ml of concentrated perchloric acid. The vigorously stirred reaction mixture remains a suspension for a short time; then a yellow gum precipitates onto the walls of the flask. The mixture is partitioned between brine/sodium bicarbonate and ethyl acetate. The ethyl acetate layer is washed with brine, dried over anhydrous sodium sulfate and evaporated, yielding 325 mg of a viscous, pale yellow oil. TLC of the crude product indicates a 1:1 mixture of enol ether and the corresponding aldehyde. The crude product is re-subjected to the same reaction conditions as described above. This time, after 1 hr, TLC shows that both the enol ether and the aldehyde have been largely converted to the titled benzofuran. An additional 30 ml tetrahydrofuran and 10 ml of 2M perchloric acid were added and stirring is continued at 25° for 90 min. TLC analysis of an aliquot (1:1 acetone/hexane) shows that the benzofuran is still the major product. Workup under conditions described above yields 300 mg of crude benzofuran, which is chromatographed on a column containing 20 g of silica gel. The column is packed and eluted (2 ml fractions) with 1:1 acetone/hexane.

Fractions 32–42 are combined and give 125 mg of pure titled benzofuran as a viscous, colorless oil which crystallizes in the refrigerator and melts just below room temperature.

The IR ($\nu$max, neat) spectrum reveals peaks at 1576, 1536, 1469, 1423, 1331, 1264, 1197, 1126, 1110, 1028, 884, 812, 769, 753, 735, and 713 cm$^{-1}$.

The NMR (CDCl$_3$, TMS, δ) spectrum reveals peaks at 8.60–8.25, 7.65–6.90, 6.70–6.55, and 4.06.

The mass spectrum reveals ions at m/e 209, 180, 166, 152, 131, 102, 90, 77, and 63.

PREPARATION 20

3-(4-Nitrophenyl)pyridine

Refer to Chart B (conversion of XX to XXI).

3-Phenylpyridine (25.0 g, 0.161 mole) is added carefully and with cooling (ice-bath) to 70% nitric acid (140 ml). The resulting solution is stirred and, when TLC (1:1 acetone-hexane) shows no reaction after 24 hr, it is heated in a 70° C. oil bath. Some reaction is observed by TLC but it is very slow and so, after 4 days, concentrated sulfuric acid (50 ml) is added. The mixture is stirred over several days at room temperature after which the starting material is entirely consumed. The solution is poured onto ice and the mixture is made alkaline by the cautious addition of 50% aqueous NaOH. The mixture is extracted 3 times with ethyl acetate. (650 ml), the combined organic layers are washed with brine, dried over MgSO$_4$, filtered, and reduced in volume to 400 ml. Crystallization occurred, giving a first crop of 13.139 g of tilted product, melting point of 145°–148° C. and, from the concentrated filtrate, a second crop of 4.16 g (total 17.299 g, 0.0865 mole, 53%) of product, melting point 143°–147° C.

PREPARATION 21

3-(4-Aminophenyl)pyridine

Refer to Chart B (conversion of XXI to XXII).

A mixture of nitropyridine, Preparation 20 (16.799 g, 0.084 mole) with 5% palladium on carbon (1 g) in absolute ethanol (500 ml) is shaken with hydrogen on a Parr hydrogenation apparatus for 1 hr during which time the hydrogen uptake ceased. TLC (1:1 acetone-hexane) shows only a new, more polar spot. The catalyst is removed by filtration, the solvent is removed under reduced pressure, and the crystalline residue is recrystallized from methylene chloride-hexane, giving the tilted product as a first crop, 8.470 g, melting point 119°–120° C.; a second crop, 4.635 g, melting point 117°–119° C.; and a third crop, 0.980 g (total 14.085 g, 0.0827 mole, 98%), melting point 113°–117° C.

PREPARATION 22

4-(3-Pyridyl)phenol

Refer to Chart B (conversion of XXII to XXIII).

Using the procedure described above, 3-(4'-aminophenyl)pyridine (10.0 g, 0.059 mol) is converted to the phenol. A total of 7.66 g of product is obtained, after chromatography, which is then recrystallized from acetone-hexane to give 6.52 g (65% of theory) of off-white crystals which have as melting point of 202°–203° C.

The C:H:N ratio is 76.71:5.42:8.13; when repeated, it is 76.76:5.30:8.18.

The IR (mull) spectrum reveals peaks at 2688, 2652, 2624, 2455, 1608, 1595, 1583, 1525, 1292, 1274, 1251, 1180, 842, 830, and 812 cm$^{-1}$.

The high resolution mass spectrum yields ions at m/e 171.0690, 154, 142, and 115.

PREPARATION 23

2-Formyl-4-(3-pyridyl)phenol

Refer to Chart B (conversion of XXIII to XXIV).

The formylation procedure described above is followed using the phenol-pyridine of Preparation 22 (5.844 g, 0.0342 mole) with hexamethylenetetramine (5.3 g) in trifluoroacetic acid (60 ml). Following workup, the crude product is chromatographed over silica gel (200 g) packed as a slurry in 40% acetone-hexane. The crude product is applied to the column in 75% acetone-hexane and the column is eluted with 40% acetone-hexane. Fractions of 200 ml volume are collected. Fractions 4–10 contain the major product and are pooled. Crystallization from acetone-hexane gives a first crop of 2.090 g, melting point 111°–113° C., and a second crop of 0.533 g, melting point of 111°–120° C. TLC (1:1 acetone-hexane) of the second crop shows the presence of two components. The first crop is dissolved in acetone and after addition of hexane was filtered to remove a cloudy precipitate. The filtrate is cooled in a freezer, giving light yellow crystals, melting point 122°–123° C. An additional recrystallization from acetone-hexane gives an analytical sample of the titled product as very pale yellow crystals with a melting point of 123°–124° C. The IR (Nujol) spectrum reveals peaks at 2567, 1674, 1608, 1308, 1290, 1259, 1241, 1196, 1166, 1117, 1034, and 810 cm$^{-1}$. The NMR (CDCl$_3$, $\delta$) spectrum reveals peaks at 10.03, 8.86, 8.64, and 7.95–7.05.

The C:H:N ratio is 72.27:4.59:703.

EXAMPLE 23

Ethyl 5-(3-pyridyl)-2-benzofurancarboxylate (Formula I, Z$_1$ is 3-pyridyl, X$_1$ is a valence bond (i.e., n is zero) and is para to the oxygen, R$_9$ and R$_{12}$ are hydrogen, D is a double bond, and R$_7$ is —COOCH$_2$CH$_3$)

Refer to Chart A (conversion of X to XV).

Using sodium hydride (1.01 g of 59.6% sodium hydride dispersion, 25 mmol NaH), diethylbromomalonate (2.53 g, 10.6 mmol), and dicyclohexyl-18-crown-6 (24 drops), the phenol aldehyde of Preparation 29 (1.80 g, 9.6 mmol) is converted to the benzofuran by the procedure described above. A total of 1.58 g (61% of theory) of the product is obtained as a solid after chromatography on silica gel using 20% acetone-hexane. The product is recrystallized from acetone-hexane twice to give 1.33 g, melting point of 91°–92° C.

Anal. Calcd. for C$_{16}$H$_{13}$NO$_3$: C, 71.90; H, 4.90; N, 5.24. The C:H:N ratio is 71.91:4.88:5.27.

The mass spectrum reveals ions at m/e 267.0888, 239, 222, 195, and 166.

The IR (Nujol) spectrum reveals peaks at 1723, 1567, 1312, 1221, 1173, 950, 882, 844, 831, and 812 cm$^{-1}$.

The NMR (CDCl$_3$, $\delta$) spectrum reveals peaks at 8.87, 8.63, 7.67. 4/46. amd 1.44.

EXAMPLE 24

Sodium 5-(3-pyridyl)-2-benzofurancarboxylate (formula I, Z$_2$ is 3-pyridyl, X$_1$ is a valence bond and is para to the oxygen, R$_9$ and R$_{12}$ are hydrogen, D is a double bond, and R$_7$ is —COONa) (The sodium salt of Example 27)

A solution of ethyl 5-(3-pyridyl)-2-benzofuran carboxylate (1.21 g, 4.53 mmol) in methanol (15 ml) is treated with a solution of 5 ml of 1N NaOH and 10 ml of water. The reaction is stirred at room temperature for 16 hr and found to be complete by TLC evidence. The methanol-water is removed under reduced pressure to give a white solid. The solid is recrystallized twice from water-acetone to give 0.928 g, melting point of greater 290° C.

The IR (mull) spectrum reveals peaks at 3493, 3380, 1633, 1609, 1513, 1574, 1256, 1168, 1131, 944, 880, and 809 cm$^{-1}$.

The mass spectrum reveals ions at m/e 195 and 44.

The NMR (D$_2$O, $\delta$) spectrum reveals peaks at 8.25 and 7.30.

The C:H:N ratio is 58.03:3.07:4.84; when repeated it is 58.60:3.33:4.73.

PREPARATION 24

Ethyl 5-formylbenzofuran-2-carboxylate and Ethyl 4-formylbenzofuran-2-carboxylate Refer to Chart G (conversion of XCVII to XCVIII).

To 10 ml of absolute ethanol under a nitrogen atmosphere is added 0.40 g (17.4 mmol) of sodium metal in small pieces over 2–3 min. When gas evolution has ceased and all of the sodium has dissolved, 2-nitropropane (1.55 ml, 16.2 mmol) is added via syringe in one portion. Almost immediately a white precipitate forms which stops the sitrring bar. This is broken up by a spatula to give a milky suspension. The resulting magnetically stirred mixture is heated to 65° C. for 30 min under a nitrogen atmosphere. To this mixture is added a solution of the starting material dissolved in 20 ml of absolute ethanol. After stirring at 65° C. for 3 hr TLC analysis indicates only a trace of starting material remaining. The reaction is quenched by the addition of saturated aqueous ammonium chloride and ethanol is removed under reduced pressure. The concentrate is diluted with 25 ml of brine and extracted with chloroform (75 ml). This results in an emulsion which can not be broken up. Consequently this mixture is filtered through a Celite pad and the filtrate is diluted with 25 ml brine and equilibrated. The organic layer is drawn off and the aqueous wash is extracted twice with 50 ml portions of chloroform. The organic layers are combined, dried (MgSO$_4$), filtered and concentrated to give 3.19 g of crude titled product as a yellow oil.

The crude product is chromatographed on 192 g of HPLC grade silica gel eluting with hexane-acetone (6:1) and collecting 50 ml fractions. Fractions 10–12 contain a residual amount of unreacted starting material. Partial separation of the aldehyde isomers is observed. Fractions 13–15 afford primarily the 4-formyl isomers, fractions 16–18 give approximately a 1:1 mixture and fractions 19–24 give primarily the 5-formyl derivative. Altogether 2.26 g (77%) of a mixture of isomeric products is obtained. Fraction 19 (essentially pure ethyl 5-formylbenzofuran-2-carboxylate) is set aside for analysis. This material later solidifies and is recrystallized from ethyl acetate/hexane to give white needles with a melting point of 101°–102° C.

The NMR (CDCl$_3$; TMS, δ) spectrum reveals peaks at 10.20, 8.37–7.58, 4.50, and 1.47.

The IR (Nujol, νmax) spectrum reveals peaks at 1726, 1692, 1615, 1588, 1570, 1400, 1350, 1322, 1300, 1266, 1220, 1198, 1145, 1116, 1100, 1021, 949, 940, 919, 842, 834, 781, 767, 750 and 683 cm$^{-1}$.

The mass spectrum reveals ions at m/e 218.0588, 203, 189, 173, 161, 146, and 117.

The C:H ratio is 66.03:4.64

EXAMPLE 25

Ethyl 5-[(3'-pyridinyl)hydroxymethyl]-benzofuran-2-carboxylate and Ethyl 4-[(3'-pyridinyl)-hydroxymethyl]-benzofuran-2-carboxylate (Formula I: $Z_1$ is 3-pyridinyl, $X_1$ is —CH(OH)— and is para or meta to the oxygen, $R_9$ and $R_{12}$ are hydrogen, D is a double bond, m is zero, and $R_7$ is —COOCH$_2$CH$_3$)

Refer to Chart G (conversion of XCVIII to CI).

A 500 ml 3-neck (24/40) round bottomed flask, equipped with a nitrogen inlet and a mechanical stirrer, is charged with 2.12 ml (22.1 mmol) of 3-bromopyridine ethyl ether (200 ml, dried over molecular sieves) is added and the resulting solution was cooled to −78° C. under a nitrogen atmosphere. n-Butyllithium (15 ml, 23 mmol) is added to the stirred solution via syringe over 2–3 min to give a pale yellow milky suspension. After stirring for 30 min, a solution of the aldehyde mixture (Preparation 24) in 25 ml of anhydrous ether is added in one portion (approximately 2 ml of tetrahydrofuran is added initially to the aldehyde mixture to get it to dissolve). A dull tan colored milky suspension results and is stirred at −78° C. for one hr. Saturated aqueous ammonium chloride (25 ml) is added to quench the reaction. The mixture is allowed to warm to room temperature and ether is removed under reduced pressure. The concentrate is diluted with chloroform and washed twice with brine (100 ml), dried (MgSO$_4$), filtered and concentrated to give 2.77 g of crude product as an orange colored oil.

This material is chromatographed on 192 g of HPLC grade silica gel, eluting with hexane-ethyl acetate (7:3) (+5% ethanol), collecting 40 ml fractions. Fractions 53–62 are homogeneous by TLC and are combined and concentrated to give 0.194 g of the 7-pyridinyl product as a yellow oil. Similarly fractions 63–67 afford 0.071 g of a mixture and fractions 68–103 afford 0.837 g of the 5-pyridinyl product as a yellow oil. The NMR spectrum of the title product indicates some impurities present and the material is rechromatographed over 6.7 g HPLC grade silica gel, eluting with hexane-acetone (4:1) and collecting 10 ml fractions. The fractions are combined and concentrated to give 0.180 g of pure 4-pyridinyl product, with a combined yield of 51%. Spectral data for this product is as follows:

The NMR (CDCl$_3$; TMS, δ) spectrum reveals peaks at 8.57–7.10, 6.11, 5.70, 4.39 and 1.38.

The IR (film, νmax) spectrum reveals peaks at 3152, 2984, 1724, 1611, 1594, 1571, 1562, 1478, 1425, 1393, 1372, 1329, 1309, 1261, 1183, 1154, 1104, 1070, 1040, 1028, 1020, 979, 951, 856, 791, 763, 713, 666 and 633 cm$^{-1}$.

The mass spectrum reveals ions at m/e 297.1020, 280, 252, 224, 196, 191, 167, 145, 119, 106, 91, and 79.

For the 5-pyridinyl product, spectral data is as follows:

The NMR (CDCl$_3$; TMS, δ) spectrum reveals peaks at 8.55–7.04, 6.0, 5.90, 4.39, and 1.39.

The IR (film, νmax) spectrum reveals peaks at 2923, 2856, 1720, 1576, 1562, 1464, 1456, 1373, 1347, 1322, 1294, 1268, 1229, 1192, 1140, 1120, 1094, 1063, 1040, 1027, 1019, 945, 945, 937, 893, 842, 810, 766, 748, 716, 690, 679, 649, 632, and 610 cm$^{-1}$.

The mass spectrum reveals ions at m/e 297.1014, 280, 268, 252, 224, 219, 191, 119, 106, and 91.

The C:H:N ratio is 68.43:5.12:4.83.

EXAMPLE 26

Sodium 5-[(3'-pyridinyl)hydroxymethyl]-benzofuran-2-carboxylate (Formula I: $Z_1$ is 3-pyridinyl, $X_1$ is —CH(OH)— and is para to oxygen, $R_9$ and $R_{12}$ are hydrogen, D is a double bond, m is zero, $Y_1$ is —O—, and $R_7$ is —COONa)

The ethyl ester starting material (Example 25) (0.345 g, 1.16 mmol) is dissolved in 10 ml of absolute ethanol. Water (2 ml) and 1.15 ml (1.15 mml) of 1.00N NaOH reagent are added and the resulting solution is stirred at room temperature for 18 hr at which time no starting material is evident by TLC. Ethanol is removed under reduced pressure and the concentrate is diluted with 150 ml of water, washed with ethyl ether, filtered through a cotton plug, frozen and lyophilized to give 0.303 g of product as a tan colored powder.

EXAMPLE 27

Sodium 4-[(3'-pyridinyl)hydroxymethyl]-benzofuran-2-carboxylate (Formula I: $Z_1$ is 3-pyridinyl, $X_1$ is —CH(OH)— and is meta to oxygen, $R_9$ and $R_{12}$ are hydrogen, D is a double bond, m is zero, $Y_1$ is —O—, and $R_7$ is —COONa)

The ethyl esters starting material (Example 27) (0.117 g, 0.396 mmol) is dissolved in 5 ml of absolute ethanol. Water (0.5 ml) and 400 μl (0.400 mmol) of 1.0N NaOH reagent are added and the resulting solution is stirred at room temperature for 6.5 hr at which time TLC analysis shows no remaining starting material. Ethanol is removed under reduced pressure and the concentrate is diluted with 50 ml of water, filtered through a cotton plug, frozen and lyophilized to give 0.113 g of product as a white fluffy powder.
TABLE I
FORMULA
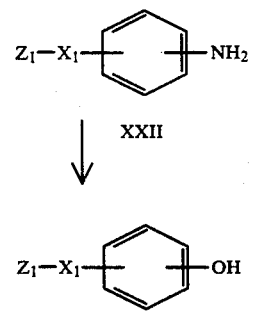
I
CHART A
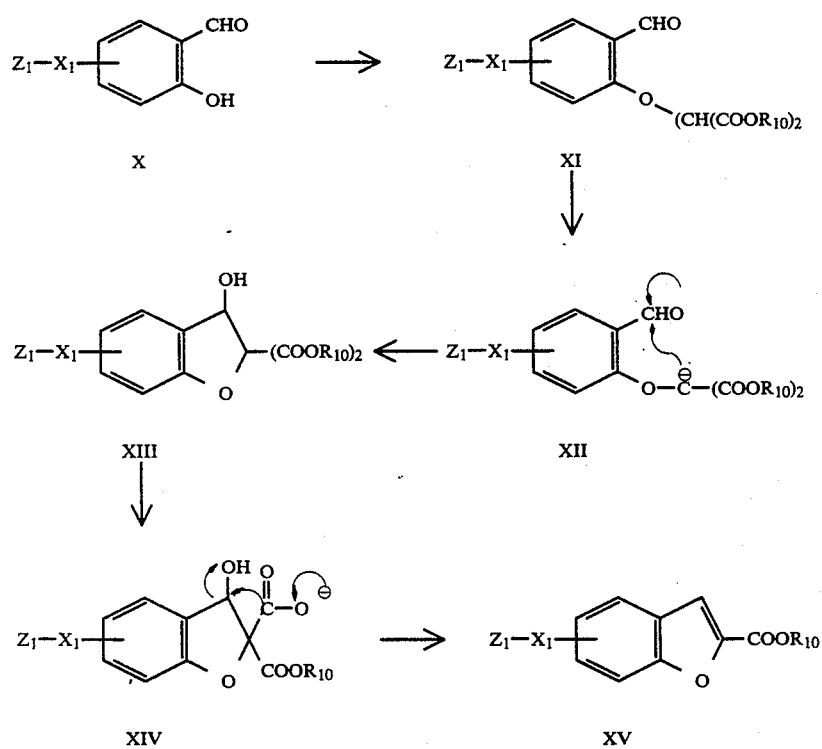
CHART B
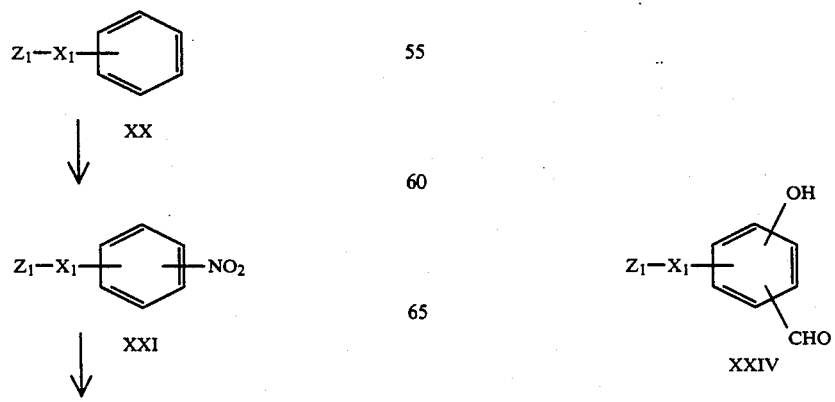
-continued
CHART B CHART C
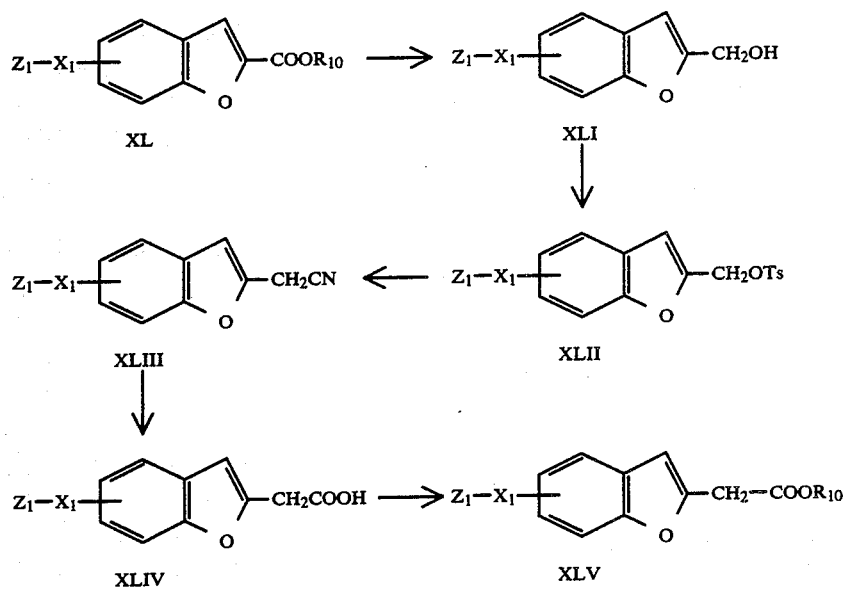
CHART D
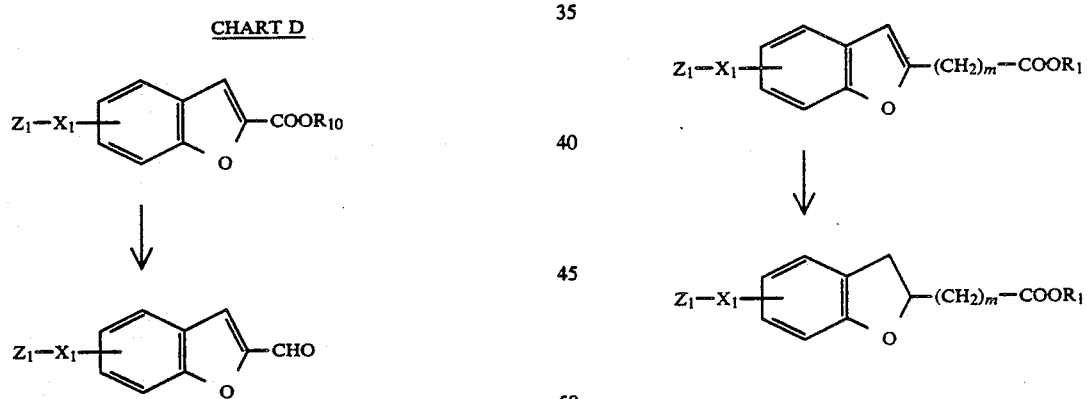
CHART E
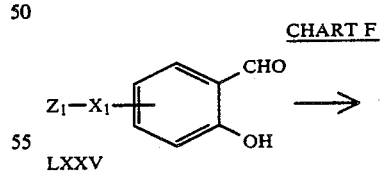
CHART F
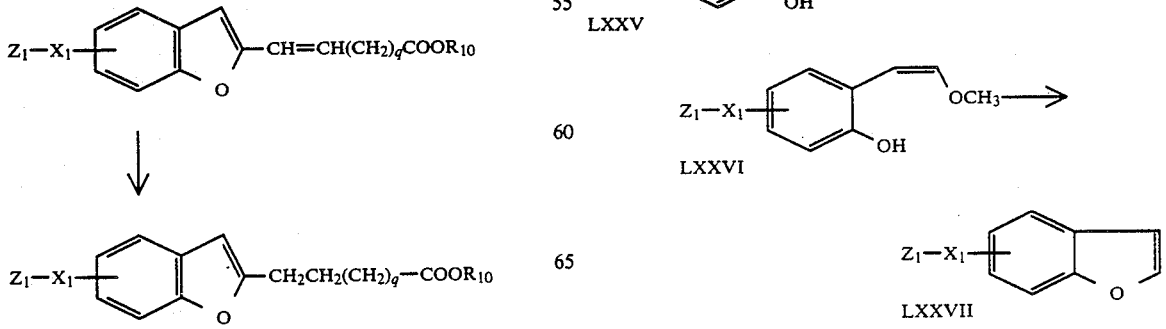

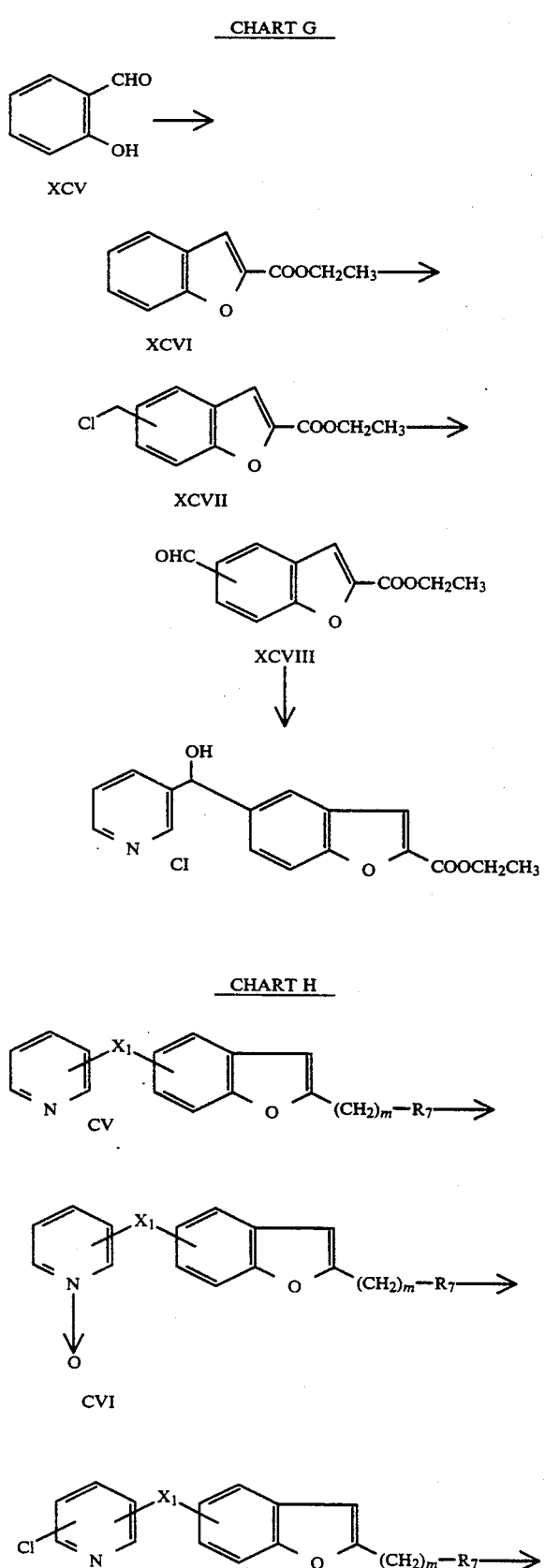
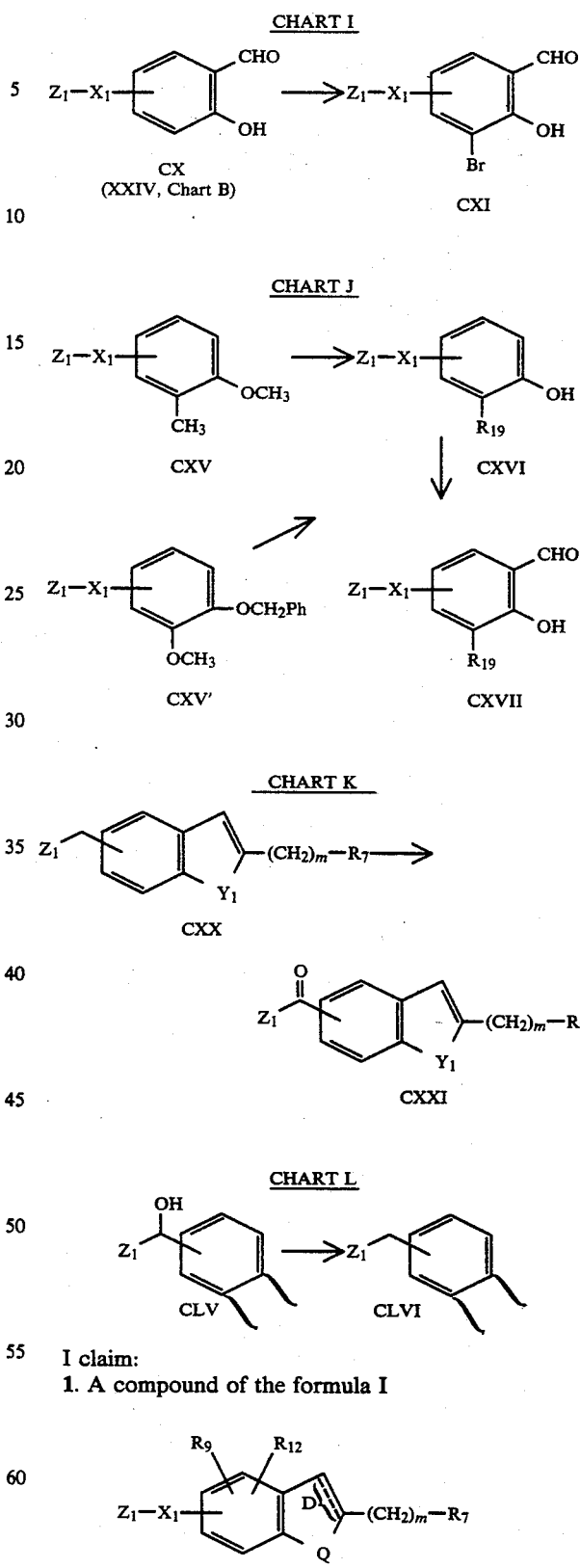
I claim:
1. A compound of the formula I
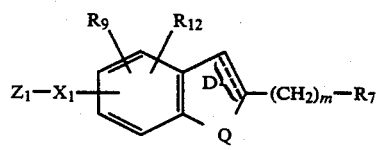
wherein $Z_1$ is
(a) 4-pyridinyl,
(b) 3-pyridinyl, or
(c) 3-pyridinyl substituted at the 4 position by (1) —OCH$_3$,
(2) —N(CH$_3$)$_2$, or
(3) NH$_2$, or
(d) 3-pyridinyl substituted at the 2, 4, 5, or 6 position by chlorine;
wherein X$_1$ is
(a) —(CH$_2$)$_n$—,
(b) —CH(OH)— or
(c) —C(O)—;
wherein R$_1$ is hydrogen, a pharmacologically acceptable cation, (C$_1$–C$_{12}$) alkyl, (C$_3$–C$_{10}$) cycloalkyl, (C$_7$–C$_{12}$) aralkyl, phenyl, phenyl mono-, di-, or trisubstituted by chloro, (C$_1$–C$_3$) alkyl, or phenyl para-substituted by
(a) —NHCO—R$_{25}$,
(b) —O—CO—R$_{26}$,
(c) —CO—R$_{24}$,
(d) —O—CO—(p-Ph)—R$_{27}$, or
(e) —CH=N—NH—CO—NH$_2$,
wherein R$_{24}$ is phenyl or acetamidophenyl, R$_{25}$ is methyl, phenyl, acetamidophenyl, benzamidophenyl, or amino, R$_{26}$ is methyl, phenyl, amino or methoxy; and R$_{27}$ is hydrogen or acetamido, and wherein —(p-Ph) is 1,4-phenylene;
wherein R$_7$ is
(a) hydrogen,
(b) —CH$_2$OH,
(c) —COOR$_1$,
(d) —CH$_2$N(R$_4$)$_2$,
(e) —CN or
(f) —C(O)—R$_4$;
wherein R$_4$ is
(a) hydrogen,
(b) (C$_1$–C$_4$)alkyl, or
(c) phenyl;
wherein R$_9$ is attached at the 7-position and is
(a) hydrogen,
(b) (C$_1$–C$_4$)alkyl
(c) fluoro,
(d) chloro,
(e) bromo, or
(f) —OCH$_3$;
wherein R$_{12}$ is hydrogen, or, R$_9$ and R$_{12}$ when taken together and attached to contiguous carbon atoms form —O—CH$_2$—O—;
wherein D represents a single or a double bond;
wherein m is an integer from 0 to 4, inclusive; and
wherein n is an integer from 0 to 1, inclusive; including, pharmacologically acceptable acid addition salts thereof with the proviso that when Z$_1$ is 4-pyridinyl or 3-pyridinyl and n is zero R$_7$ is other than hydrogen and with the further proviso that when X$_1$ is —(CH$_2$)— and m is zero, R$_7$ is other than H.

2. A compound of claim 1, selected from the group consisting of:
5-(3-pyridinyl)-2-benzofurancarboxylic acid,
7-methoxy-5-(3-pyridinylmethyl)-2-benzofurancarboxylic acid, ethyl ester,
7-methoxy-5-(3-pyridylmethyl)-2-benzofurancarboxylic acid, sodium salt,
7-bromo-5-(3-pyridylmethyl)-2-benzofurancarboxylic acid, ethyl ester,
7-bromo-5-(3-pyridylmethyl)-2-benzofurancarboxylic acid, sodium salt,
7-methyl-5-(3-pyridylmethyl)-2-benzofurancarboxylic acid, ethyl ester,
7-methyl-5-(3-pyridylmethyl)-2-benzofurancarboxylic acid, sodium salt,
ethyl 5-(3-pyridyl)-2-benzofurancarboxylate,
sodium 5-(3-pyridyl)-2-benzofurancarboxylate,
ethyl 5-[(3'-pyridinyl)hydroxymethyl]-benzofuran-2-carboxylate,
ethyl 4-[(3'-pyridinyl)hydroxymethyl]-benzofuran-2-carboxylate,
sodium 5-[(3'-pyridinyl)hydroxymethyl]-benzofuran-2-carboxylate,
2-hydroxymethyl-5-(3'-pyridinylmethyl)benzofuran,
2-hydroxymethyl-5-(3'-pyridinylmethyl)benzofuran hydrochloride, and
sodium 4-[(3'-pyridinyl)hydroxymethyl]-benzofuran-2-carboxylate.

3. A compound of claim 1, wherein D denotes a double bond, X$_1$ is —(CH$_2$)$_n$—, m is zero, R$_9$ and R$_{12}$ are hydrogen, and R$_7$ is —COOR$_1$.

4. A compound of claim 3, selected from the group consisting of:
ethyl 5-(3'-pyridinylmethyl)benzofuran-2-carboxylate,
sodium 5-(3'-pyridinylmethyl)benzofuran-2-carboxylate,
5-(3-pyridinylmethyl)-2-benzofurancarboxylic acid,
5-(3-pyridinylmethyl)-2-benzofurancarboxylic acid, hydrochloride,
5-[3-(2-chloropyridyl)methyl]-2-benzofurancarboxylic acid, ethyl ester,
5-[3-(4-chloropyridyl)methyl]-2-benzofurancarboxylic acid, ethyl ester,
5-[3-(5-chloropyridyl)methyl-2-benzofurancarboxylic acid, ethyl ester,
5-[3-(6-chloropyridyl)methyl]-2-benzofurancarboxylic acid, ethyl ester,
5-[3-(6-chloropyridyl)methyl]-2-benzofurancarboxylic acid, sodium salt,
5-[3-(2-chloropyridyl)methyl]-2-benzofurancarboxylic acid, sodium salt,
5-[3-(4-chloropyridyl)methyl]-2-benzofurancarboxylic acid, sodium salt,
ethyl 6-(3-pyridylmethyl)benzofuran-2-carboxylate,
6-(3-pyridylmethyl)benzofuran-2-carboxylic acid, sodium salt, and
6-(3-pyridylmethyl)benzofuran-2-carboxylic acid.

5. 5-(3-Pyridinyl)-2-benzofurancarboxylic acid, a compound of claim 2.

6. 7-Methoxy-5-(3-pyridinylmethyl)-2-benzofurancarboxylic acid, ethyl ester, a compound of claim 2.

7. 7-Methoxy-5-(3-pyridylmethyl)-2-benzofurancarboxylic acid, sodium salt, a compound of claim 2.

8. 7-Bromo-5-(3-pyridylmethyl)-2-benzofurancarboxylic acid, ethyl ester, a compound of claim 2.

9. 7-Bromo-5-(3-pyridylmethyl)-2-benzofurancarboxylic acid, sodium salt, a compound of claim 2.

10. 7-Methyl-5-(3-pyridylmethyl)-2-benzofurancarboxylic acid, ethyl ester, a compound of claim 2.

11. 7-Methyl-5-(3-pyridylmethyl)-2-benzofurancarboxylic acid, sodium salt, a compound of claim 2.

12. Ethyl 5-(3-pyridyl)-2-benzofurancarboxylate, a compound of claim 2.

13. Sodium 5-(3-pyridyl)-2-benzofurancarboxylate, a compound of claim 2.

14. Ethyl 5-[(3'-pyridinyl)hydroxymethyl]-benzofuran-2-carboxylate, a compound of claim 2.

15. Ethyl 4-[(3'-pyridinyl)hydroxymethyl]-benzofuran-2-carboxylate, a compound of claim 2.

16. Sodium 5-[(3'-pyridinyl)hydroxymethyl]-benzofuran-2-carboxylate, a compound of claim 2.

17. Sodium 4-[(3'-pyridinyl)hydroxymethyl]-benzofuran-2-carboxylate, a compound of claim 2.

18. Ethyl 5-(3'-pyridinylmethyl)benzofuran-2-carboxylate, a compound of claim 4.

19. Sodium 5-(3'-pyridinylmethyl)benzofuran-2-carboxylate, a compound of claim 4.

20. 2-Hydroxymethyl-5-(3'-pyridinylmethyl)benzofuran, a compound of claim 4.

21. 2-Hydroxymethyl-5-(3'-pyridinylmethyl)benzofuran hydrochloride, a compound of claim 2.

22. 5-(3-Pyridinylmethyl)-2-benzofurancarboxylic acid, a compound of claim 2.

23. 5-(3-Pyridinylmethyl)-2-benzofurancarboxylic acid, hydrochloride, a compound of claim 4.

24. 5-[3-(2-chloropyridyl)methyl]-2-benzofurancarboxylic acid, ethyl ester, a compound of claim 4.

25. 5-[3-(4-Chloropyridyl)methyl]-2-benzofurancarboxylic acid, ethyl ester, a compound of claim 4.

26. 5-[3-(5-Chloropyridyl)methyl]-2-benzofurancarboxylic acid, ethyl ester, a compound of claim 4.

27. 5-[3-(6-Chloropyridyl)methyl]-2-benzofurancarboxylic acid, ethyl ester, a compound of claim 4.

28. 5-[3-(6-Chloropyridyl)methyl]-2-benzofurancarboxylic acid, sodium salt, a compound of claim 4.

29. 5-[3-(2-Chloropyridyl)methyl]-2-benzofurancarboxylic acid, sodium salt, a compound of claim 4.

30. 5-[3-(4-Chloropyridyl)methyl]-2-benzofurancarboxylic acid, sodium salt, a compound of claim 4.

31. Ethyl 6-(3-pyridylmethyl)benzofuran-2-carboxylate, a compound of claim 4.

32. 6-(3-Pyridylmethyl)benzofuran-2-carboxylic acid, sodium salt, a compound of claim 4.

33. 6-(3-Pyridylmethyl)benzofuran-2-carboxylic acid, a compound of claim 4.

* * * * *